(12) United States Patent
Messerli et al.

(10) Patent No.: US 11,696,837 B2
(45) Date of Patent: Jul. 11, 2023

(54) INTERVERTEBRAL IMPLANT WITH FIXATION GEOMETRY

(71) Applicant: DePuy Synthes Products, Inc., Raynham, MA (US)

(72) Inventors: Dominique Messerli, Bristol, RI (US); Ryan T. Walsh, Downingtown, PA (US); Brandon L. Randall, Duxbury, MA (US); David E. Evans, Atlanta, GA (US); Jacqueline Myer, Pottstown, PA (US); David Koch, North Logan, UT (US); Markus Hunziker, Aargau (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 545 days.

(21) Appl. No.: 16/718,826

(22) Filed: Dec. 18, 2019

(65) Prior Publication Data
US 2020/0121469 A1    Apr. 23, 2020

Related U.S. Application Data

(60) Continuation of application No. 14/997,014, filed on Jan. 15, 2016, now Pat. No. 10,512,548, which is a
(Continued)

(51) Int. Cl.
*A61F 2/44* (2006.01)
*A61F 2/30* (2006.01)
(Continued)

(52) U.S. Cl.
CPC .............. *A61F 2/447* (2013.01); *A61F 2/442* (2013.01); *A61F 2/4455* (2013.01); *A61B 17/86* (2013.01);
(Continued)

(58) Field of Classification Search
None
See application file for complete search history.

(56) References Cited

U.S. PATENT DOCUMENTS

| 424,836 A | 4/1890 | Thompson |
| 438,892 A | 10/1890 | Lippy |

(Continued)

FOREIGN PATENT DOCUMENTS

| AU | 2004232317 A1 | 11/2004 |
| CA | 2111598 A1 | 6/1994 |

(Continued)

OTHER PUBLICATIONS

U.S. Appl. No. 11/199,599: Final Rejection, dated Dec. 24, 2009, 21 pages.
(Continued)

*Primary Examiner* — Jan Christopher L Merene
(74) *Attorney, Agent, or Firm* — BakerHostetler

(57) ABSTRACT

An intervertebral spacer implant (80) is provided with a retention mechanism (86) to help alleviate expulsion and movement of the implant when placed in the spine while providing an implant that is easier to insert in the spine. In one embodiment the retention mechanism comprises a keel on at least one of the inferior or superior faces of the spacer implant preferably extending in an anterior-posterior direction. In another embodiment the implant comprises a spacer (84) and a plate (82), the plate comprising a supplemental or alternative retention mechanism. In one embodiment the retention mechanism comprises one or more holes (88) in the anterior end of the plate. In yet another embodiment, the retention mechanism comprises one or more blades that are in a first position when inserted and are preferably rotated to a second position that engages the superior and inferior vertebrae.

18 Claims, 18 Drawing Sheets

Related U.S. Application Data division of application No. 14/166,979, filed on Jan. 29, 2014, now abandoned, which is a continuation of application No. 12/280,917, filed as application No. PCT/US2007/005098 on Feb. 27, 2007, now abandoned.

(60) Provisional application No. 60/838,229, filed on Aug. 16, 2006, provisional application No. 60/777,732, filed on Feb. 27, 2006, provisional application No. 60/777,663, filed on Feb. 27, 2006.

(51) Int. Cl.
  *A61B 17/86* (2006.01)
  *A61F 2/46* (2006.01)
  *A61F 2/28* (2006.01)

(52) U.S. Cl.
  CPC ............... *A61F 2/28* (2013.01); *A61F 2/4611* (2013.01); *A61F 2002/2835* (2013.01); *A61F 2002/30004* (2013.01); *A61F 2002/30187* (2013.01); *A61F 2002/30387* (2013.01); *A61F 2002/30507* (2013.01); *A61F 2002/30578* (2013.01); *A61F 2002/30579* (2013.01); *A61F 2002/30593* (2013.01); *A61F 2002/30604* (2013.01); *A61F 2002/30784* (2013.01); *A61F 2002/30843* (2013.01); *A61F 2002/30845* (2013.01); *A61F 2002/30884* (2013.01); *A61F 2002/30904* (2013.01); *A61F 2220/0025* (2013.01); *A61F 2250/0014* (2013.01); *A61F 2310/00017* (2013.01); *A61F 2310/00023* (2013.01); *A61F 2310/00179* (2013.01); *A61F 2310/00359* (2013.01)

(56) References Cited

U.S. PATENT DOCUMENTS

| | | |
|---|---|---|
| 1,105,105 A | 7/1914 | Sherman |
| 1,200,797 A | 10/1916 | Barbe |
| 2,151,919 A | 3/1939 | Jacobson |
| 2,372,888 A | 4/1945 | Duggan |
| 2,621,145 A | 12/1952 | Sano |
| 2,782,827 A | 2/1957 | Rosan |
| 2,906,311 A | 9/1959 | Boyd |
| 2,972,367 A | 2/1961 | Wootton |
| 3,062,253 A | 11/1962 | Miliheiser |
| 3,272,249 A | 9/1966 | Houston |
| 3,350,103 A | 10/1967 | Ahlstone |
| 3,426,364 A | 2/1969 | Lumb |
| 3,561,075 A | 2/1971 | Selinko |
| 3,579,831 A | 5/1971 | Stevens et al. |
| 3,707,303 A | 12/1972 | Petri |
| 3,810,703 A | 5/1974 | Pasbrig |
| 3,867,728 A | 2/1975 | Stubstad et al. |
| 3,899,897 A | 8/1975 | Boerger et al. |
| 3,945,671 A | 3/1976 | Gerlach |
| 4,017,946 A | 4/1977 | Soja |
| 4,056,301 A | 11/1977 | Norden |
| 4,123,132 A | 10/1978 | Hardy et al. |
| 4,135,506 A | 1/1979 | Ulrich |
| 4,278,120 A | 7/1981 | Hart et al. |
| 4,280,875 A | 7/1981 | Werres |
| 4,285,377 A | 8/1981 | Hart |
| 4,288,902 A | 9/1981 | Franz |
| 4,297,063 A | 10/1981 | Hart |
| 4,298,993 A | 11/1981 | Kovaleva et al. |
| 4,299,902 A | 11/1981 | Soma et al. |
| 4,349,921 A | 9/1982 | Kuntz |
| 4,388,921 A | 6/1983 | Sutter et al. |
| 4,394,370 A | 7/1983 | Jefferies |
| 4,450,591 A | 5/1984 | Rappaport |
| 4,484,570 A | 11/1984 | Sutter et al. |
| 4,488,543 A | 12/1984 | Tornier |
| 4,501,269 A | 2/1985 | Bagby |
| 4,503,848 A | 3/1985 | Caspar et al. |
| 4,512,038 A | 4/1985 | Alexander et al. |
| 4,545,374 A | 10/1985 | Jacobson |
| 4,553,890 A | 11/1985 | Gulistan |
| 4,599,086 A | 7/1986 | Doty |
| 4,627,853 A | 12/1986 | Campbell et al. |
| 4,640,524 A | 2/1987 | Sedlmair |
| 4,648,768 A | 3/1987 | Hambric |
| 4,678,470 A | 7/1987 | Nashef et al. |
| 4,708,377 A | 11/1987 | Hunting |
| 4,711,760 A | 12/1987 | Blaushild |
| 4,714,469 A | 12/1987 | Kenna |
| 4,717,115 A | 1/1988 | Schmitz et al. |
| 4,743,256 A | 5/1988 | Brantigan |
| 4,781,721 A | 11/1988 | Grundei |
| 4,793,335 A | 12/1988 | Frey et al. |
| 4,804,290 A | 2/1989 | Balsells |
| 4,812,094 A | 3/1989 | Grube |
| 4,829,152 A | 5/1989 | Rostoker et al. |
| 4,834,757 A | 5/1989 | Brantigan |
| 4,858,603 A | 8/1989 | Clemow et al. |
| 4,872,452 A | 10/1989 | Alexson |
| 4,878,915 A | 11/1989 | Brantigan |
| 4,904,261 A | 2/1990 | Dove et al. |
| 4,917,704 A | 4/1990 | Frey et al. |
| 4,932,973 A | 6/1990 | Gendler |
| 4,936,851 A | 6/1990 | Fox et al. |
| 4,946,378 A | 8/1990 | Hirayama et al. |
| 4,950,296 A | 8/1990 | McIntyre |
| 4,955,908 A | 9/1990 | Frey et al. |
| 4,961,740 A | 10/1990 | Ray et al. |
| 4,976,576 A | 12/1990 | Mahaney et al. |
| 4,978,350 A | 12/1990 | Wagenknecht |
| 4,994,084 A | 2/1991 | Brennan |
| 4,997,432 A | 3/1991 | Keller |
| 5,006,120 A | 4/1991 | Carter |
| 5,010,783 A | 4/1991 | Sparks et al. |
| 5,017,069 A | 5/1991 | Stengel |
| 5,020,949 A | 6/1991 | Davidson et al. |
| 5,026,373 A | 6/1991 | Ray et al. |
| 5,030,220 A | 7/1991 | Howland |
| 5,047,058 A | 9/1991 | Roberts et al. |
| 5,053,049 A | 10/1991 | Campbell |
| 5,062,850 A | 11/1991 | MacMillan et al. |
| 5,071,437 A | 12/1991 | Steffee |
| 5,084,051 A | 1/1992 | Toermaelae et al. |
| 5,085,660 A | 2/1992 | Lin |
| 5,096,150 A | 3/1992 | Westwood |
| 5,108,438 A | 4/1992 | Stone |
| 5,112,354 A | 5/1992 | Sires |
| 5,116,374 A | 5/1992 | Stone |
| 5,118,235 A | 6/1992 | Dill |
| 5,139,424 A | 8/1992 | Yli-Urpo |
| 5,147,404 A | 9/1992 | Downey |
| 5,163,949 A | 11/1992 | Bonutti |
| 5,163,960 A | 11/1992 | Bonutti |
| 5,180,381 A | 1/1993 | Aust et al. |
| 5,192,327 A | 3/1993 | Brantigan |
| 5,197,971 A | 3/1993 | Bonutti |
| 5,201,736 A | 4/1993 | Strauss |
| 5,207,543 A | 5/1993 | Kirma |
| 5,211,664 A | 5/1993 | Tepic et al. |
| 5,235,034 A | 8/1993 | Bobsein et al. |
| 5,238,342 A | 8/1993 | Stencel |
| 5,258,031 A | 11/1993 | Salib et al. |
| 5,269,785 A | 12/1993 | Bonutti |
| 5,275,601 A | 1/1994 | Gogolewski et al. |
| 5,281,226 A | 1/1994 | Davydov et al. |
| 5,282,861 A | 2/1994 | Kaplan |
| 5,284,655 A | 2/1994 | Bogdansky et al. |
| 5,290,312 A | 3/1994 | Kojimoto et al. |
| 5,295,994 A | 3/1994 | Bonutti |
| 5,298,254 A | 3/1994 | Prewett et al. |
| 5,304,021 A | 4/1994 | Oliver et al. |
| 5,306,307 A | 4/1994 | Senter et al. |
| 5,306,308 A | 4/1994 | Gross et al. |
| 5,306,309 A | 4/1994 | Wagner et al. |

(56) References Cited

U.S. PATENT DOCUMENTS

| | | |
|---|---|---|
| 5,314,476 A | 5/1994 | Prewett et al. |
| 5,314,477 A | 5/1994 | Marnay |
| 5,329,846 A | 7/1994 | Bonutti |
| 5,330,535 A | 7/1994 | Moser et al. |
| 5,331,975 A | 7/1994 | Bonutti |
| 5,345,927 A | 9/1994 | Bonutti |
| 5,348,788 A | 9/1994 | White |
| 5,368,593 A | 11/1994 | Stark |
| 5,380,323 A | 1/1995 | Howland |
| 5,385,583 A | 1/1995 | Cotrel |
| 5,397,364 A | 3/1995 | Kozak et al. |
| 5,403,317 A | 4/1995 | Bonutti |
| 5,403,348 A | 4/1995 | Bonutti |
| 5,405,391 A | 4/1995 | Henderson et al. |
| 5,411,348 A | 5/1995 | Balsells |
| 5,423,817 A | 6/1995 | Lin |
| 5,425,772 A | 6/1995 | Brantigan |
| 5,431,658 A | 7/1995 | Moskovich |
| 5,439,684 A | 8/1995 | Prewett et al. |
| 5,441,538 A | 8/1995 | Bonutti |
| 5,443,514 A | 8/1995 | Steffee |
| 5,443,515 A | 8/1995 | Cohen et al. |
| 5,454,365 A | 10/1995 | Bonutti |
| 5,458,638 A | 10/1995 | Kuslich et al. |
| 5,458,641 A | 10/1995 | Ramirez Jimenez |
| 5,458,643 A | 10/1995 | Oka et al. |
| 5,464,426 A | 11/1995 | Bonutti |
| 5,478,342 A | 12/1995 | Kohrs |
| 5,484,437 A | 1/1996 | Michelson |
| 5,487,744 A | 1/1996 | Howland |
| 5,489,308 A | 2/1996 | Kuslich et al. |
| 5,496,348 A | 3/1996 | Bonutti |
| 5,507,818 A | 4/1996 | McLaughlin |
| 5,514,153 A | 5/1996 | Bonutti |
| 5,514,180 A | 5/1996 | Heggeness et al. |
| 5,520,690 A | 5/1996 | Errico et al. |
| 5,522,846 A | 6/1996 | Bonutti |
| 5,522,899 A | 6/1996 | Michelson |
| 5,527,343 A | 6/1996 | Bonutti |
| 5,531,746 A | 7/1996 | Errico et al. |
| 5,534,012 A | 7/1996 | Bonutti |
| 5,534,030 A | 7/1996 | Navarro et al. |
| 5,534,031 A | 7/1996 | Matsuzaki et al. |
| 5,534,032 A | 7/1996 | Hodorek |
| 5,545,222 A | 8/1996 | Bonutti |
| 5,545,842 A | 8/1996 | Balsells |
| 5,549,612 A | 8/1996 | Yapp et al. |
| 5,549,630 A | 8/1996 | Bonutti |
| 5,549,631 A | 8/1996 | Bonutti |
| 5,549,679 A | 8/1996 | Kuslich |
| 5,550,172 A | 8/1996 | Regula et al. |
| 5,554,191 A | 9/1996 | Lahille et al. |
| 5,556,430 A | 9/1996 | Gendler |
| 5,556,431 A | 9/1996 | Buttner-Janz |
| 5,569,305 A | 10/1996 | Bonutti |
| 5,569,308 A | 10/1996 | Sottosanti |
| 5,570,983 A | 11/1996 | Hollander |
| 5,571,109 A | 11/1996 | Bertagnoli |
| 5,571,190 A | 11/1996 | Ulrich et al. |
| 5,571,192 A | 11/1996 | Schonhoffer |
| 5,577,517 A | 11/1996 | Bonutti |
| 5,578,034 A | 11/1996 | Estes |
| 5,584,862 A | 12/1996 | Bonutti |
| 5,593,409 A | 1/1997 | Michelson |
| 5,593,425 A | 1/1997 | Bonutti et al. |
| 5,597,278 A | 1/1997 | Peterkort |
| 5,601,553 A | 2/1997 | Trebing et al. |
| 5,601,554 A | 2/1997 | Howland et al. |
| 5,607,428 A | 3/1997 | Lin |
| 5,607,474 A | 3/1997 | Athanasiou et al. |
| 5,609,635 A | 3/1997 | Michelson |
| 5,609,636 A | 3/1997 | Kohrs et al. |
| 5,609,637 A | 3/1997 | Biedermann et al. |
| 5,616,144 A | 4/1997 | Yapp et al. |
| 5,620,448 A | 4/1997 | Puddu |
| 5,624,462 A | 4/1997 | Bonutti |
| 5,642,960 A | 7/1997 | Salice |
| 5,645,596 A | 7/1997 | Kim et al. |
| 5,645,606 A | 7/1997 | Oehy et al. |
| 5,653,708 A | 8/1997 | Howland |
| 5,662,710 A | 9/1997 | Bonutti |
| 5,667,520 A | 9/1997 | Bonutti |
| 5,669,909 A | 9/1997 | Zdeblick et al. |
| 5,674,296 A | 10/1997 | Bryan et al. |
| 5,676,666 A | 10/1997 | Oxland et al. |
| 5,676,699 A | 10/1997 | Gogolewski et al. |
| 5,681,311 A | 10/1997 | Foley et al. |
| 5,683,216 A | 11/1997 | Erbes |
| 5,683,394 A | 11/1997 | Rinner |
| 5,683,463 A | 11/1997 | Godefroy et al. |
| 5,685,826 A | 11/1997 | Bonutti |
| 5,694,951 A | 12/1997 | Bonutti |
| 5,702,449 A | 12/1997 | McKay |
| 5,702,451 A | 12/1997 | Biedermann et al. |
| 5,702,453 A | 12/1997 | Rabbe et al. |
| 5,702,455 A | 12/1997 | Saggar |
| 5,707,390 A | 1/1998 | Bonutti |
| 5,713,899 A | 2/1998 | Marnay et al. |
| 5,713,900 A | 2/1998 | Benzel et al. |
| 5,716,325 A | 2/1998 | Bonutti |
| 5,725,531 A | 3/1998 | Shapiro |
| 5,725,588 A | 3/1998 | Errico et al. |
| 5,728,159 A | 3/1998 | Stroever et al. |
| 5,733,306 A | 3/1998 | Bonutti |
| 5,735,853 A | 4/1998 | Olerud |
| 5,735,875 A | 4/1998 | Bonutti et al. |
| 5,735,905 A | 4/1998 | Parr |
| 5,755,796 A | 5/1998 | Ibo et al. |
| 5,755,798 A | 5/1998 | Papavero et al. |
| 5,766,251 A | 6/1998 | Koshino |
| 5,766,252 A | 6/1998 | Henry et al. |
| 5,766,253 A | 6/1998 | Brosnahan, III |
| 5,772,661 A | 6/1998 | Michelson |
| 5,776,194 A | 7/1998 | Mikol et al. |
| 5,776,196 A | 7/1998 | Matsuzaki et al. |
| 5,776,197 A | 7/1998 | Rabbe et al. |
| 5,776,198 A | 7/1998 | Rabbe et al. |
| 5,776,199 A | 7/1998 | Michelson |
| 5,778,804 A | 7/1998 | Read |
| 5,782,915 A | 7/1998 | Stone |
| 5,782,919 A | 7/1998 | Zdeblick et al. |
| 5,785,710 A | 7/1998 | Michelson |
| 5,800,433 A | 9/1998 | Benzel et al. |
| 5,827,318 A | 10/1998 | Bonutti |
| 5,836,948 A | 11/1998 | Zucherman et al. |
| 5,845,645 A | 12/1998 | Bonutti |
| 5,860,973 A | 1/1999 | Michelson |
| 5,860,997 A | 1/1999 | Bonutti |
| 5,861,041 A | 1/1999 | Tienboon |
| 5,865,845 A | 2/1999 | Thalgott |
| 5,865,849 A | 2/1999 | Stone |
| 5,872,915 A | 2/1999 | Dykes et al. |
| 5,876,402 A | 3/1999 | Errico et al. |
| 5,876,452 A | 3/1999 | Athanasiou et al. |
| 5,879,389 A | 3/1999 | Koshino |
| 5,885,299 A | 3/1999 | Winslow et al. |
| 5,888,196 A | 3/1999 | Bonutti |
| 5,888,219 A | 3/1999 | Bonutti |
| 5,888,222 A | 3/1999 | Coates et al. |
| 5,888,223 A | 3/1999 | Bray, Jr. |
| 5,888,224 A | 3/1999 | Beckers et al. |
| 5,888,227 A | 3/1999 | Cottle |
| 5,895,426 A | 4/1999 | Scarborough et al. |
| 5,899,939 A | 5/1999 | Boyce et al. |
| 5,902,303 A | 5/1999 | Eckhof et al. |
| 5,902,338 A | 5/1999 | Stone |
| 5,904,683 A | 5/1999 | Pohndorf et al. |
| 5,904,719 A | 5/1999 | Errico et al. |
| 5,906,616 A | 5/1999 | Pavlov et al. |
| 5,910,315 A | 6/1999 | Stevenson et al. |
| 5,911,758 A | 6/1999 | Oehy et al. |
| 5,920,312 A | 7/1999 | Wagner et al. |
| 5,922,027 A | 7/1999 | Stone |
| 5,928,267 A | 7/1999 | Bonutti et al. |

(56) References Cited

U.S. PATENT DOCUMENTS

| | | |
|---|---|---|
| 5,931,838 A | 8/1999 | Vito |
| 5,935,131 A | 8/1999 | Bonutti |
| 5,941,900 A | 8/1999 | Bonutti |
| 5,944,755 A | 8/1999 | Stone |
| 5,951,558 A | 9/1999 | Fiz |
| 5,954,722 A | 9/1999 | Bono |
| 5,954,739 A | 9/1999 | Bonutti |
| 5,958,314 A | 9/1999 | Draenert |
| 5,964,807 A | 10/1999 | Gan et al. |
| 5,968,098 A | 10/1999 | Winslow |
| 5,972,031 A | 10/1999 | Biedermann et al. |
| 5,972,368 A | 10/1999 | McKay |
| 5,976,141 A | 11/1999 | Haag et al. |
| 5,976,187 A | 11/1999 | Richelsoph |
| 5,980,522 A | 11/1999 | Koros et al. |
| 5,981,828 A | 11/1999 | Nelson et al. |
| 5,984,967 A | 11/1999 | Zdeblick et al. |
| 5,989,289 A | 11/1999 | Coates et al. |
| 6,001,099 A | 12/1999 | Huebner |
| 6,008,433 A | 12/1999 | Stone |
| 6,010,525 A | 1/2000 | Bonutti et al. |
| 6,013,853 A | 1/2000 | Athanasiou et al. |
| 6,017,305 A | 1/2000 | Bonutti |
| 6,017,345 A | 1/2000 | Richelsoph |
| 6,025,538 A | 2/2000 | Yaccarino et al. |
| 6,033,405 A | 3/2000 | Winslow et al. |
| 6,033,438 A | 3/2000 | Bianchi et al. |
| 6,039,762 A | 3/2000 | McKay |
| 6,042,596 A | 3/2000 | Bonutti |
| 6,045,579 A | 4/2000 | Hochschuler et al. |
| 6,045,580 A | 4/2000 | Scarborough et al. |
| 6,056,749 A | 5/2000 | Kuslich |
| 6,059,817 A | 5/2000 | Bonutti et al. |
| 6,066,175 A | 5/2000 | Henderson et al. |
| 6,077,292 A | 6/2000 | Bonutti |
| 6,080,158 A | 6/2000 | Lin |
| 6,080,193 A | 6/2000 | Hochschuler et al. |
| 6,086,593 A | 7/2000 | Bonutti |
| 6,086,614 A | 7/2000 | Mumme |
| 6,090,998 A | 7/2000 | Grooms et al. |
| 6,096,080 A | 8/2000 | Nicholson et al. |
| 6,096,081 A | 8/2000 | Grivas et al. |
| 6,099,531 A | 8/2000 | Bonutti |
| 6,102,928 A | 8/2000 | Bonutti |
| 6,110,482 A | 8/2000 | Khouri et al. |
| 6,113,637 A | 9/2000 | Gill et al. |
| 6,113,638 A | 9/2000 | Williams et al. |
| 6,120,503 A | 9/2000 | Michelson |
| 6,123,731 A | 9/2000 | Boyce et al. |
| 6,129,763 A | 10/2000 | Chauvin et al. |
| 6,132,472 A | 10/2000 | Bonutti |
| 6,136,001 A | 10/2000 | Michelson |
| 6,139,550 A | 10/2000 | Michelson |
| RE36,974 E | 11/2000 | Bonutti |
| 6,143,030 A | 11/2000 | Schroder |
| 6,143,033 A | 11/2000 | Paul et al. |
| 6,146,421 A | 11/2000 | Gordon et al. |
| 6,156,070 A | 12/2000 | Incavo et al. |
| 6,159,215 A | 12/2000 | Urbahns et al. |
| 6,159,234 A | 12/2000 | Bonutti et al. |
| 6,171,236 B1 | 1/2001 | Bonutti |
| 6,171,299 B1 | 1/2001 | Bonutti |
| 6,174,313 B1 | 1/2001 | Bonutti |
| 6,187,023 B1 | 2/2001 | Bonutti |
| 6,193,721 B1 | 2/2001 | Michelson |
| 6,193,756 B1 | 2/2001 | Studer et al. |
| 6,193,757 B1 | 2/2001 | Foley et al. |
| 6,200,347 B1 | 3/2001 | Anderson et al. |
| 6,203,565 B1 | 3/2001 | Bonutti et al. |
| 6,206,922 B1 | 3/2001 | Zdeblick et al. |
| 6,217,617 B1 | 4/2001 | Bonutti |
| 6,224,602 B1 | 5/2001 | Hayes |
| 6,231,592 B1 | 5/2001 | Bonutti et al. |
| 6,231,610 B1 | 5/2001 | Geisler |
| 6,235,033 B1 | 5/2001 | Brace et al. |
| 6,235,034 B1 | 5/2001 | Bray |
| 6,235,059 B1 | 5/2001 | Benezech et al. |
| 6,241,731 B1 | 6/2001 | Fiz |
| 6,241,769 B1 | 6/2001 | Nicholson et al. |
| 6,245,108 B1 | 6/2001 | Biscup |
| 6,258,089 B1 | 7/2001 | Campbell et al. |
| 6,258,125 B1 | 7/2001 | Paul et al. |
| 6,261,291 B1 | 7/2001 | Talaber et al. |
| 6,261,586 B1 | 7/2001 | McKay |
| 6,264,695 B1 | 7/2001 | Stoy |
| 6,270,528 B1 | 8/2001 | McKay |
| 6,277,136 B1 | 8/2001 | Bonutti |
| 6,287,325 B1 | 9/2001 | Bonutti |
| 6,306,139 B1 | 10/2001 | Fuentes |
| 6,322,562 B1 | 11/2001 | Wolter |
| 6,331,179 B1 | 12/2001 | Freid et al. |
| 6,342,074 B1 | 1/2002 | Simpson |
| 6,358,266 B1 | 3/2002 | Bonutti |
| 6,361,565 B1 | 3/2002 | Bonutti |
| 6,364,880 B1 | 4/2002 | Michelson |
| 6,368,343 B1 | 4/2002 | Bonutti et al. |
| 6,371,986 B1 | 4/2002 | Bagby |
| 6,371,987 B1 * | 4/2002 | Weiland ............... A61F 2/4455 623/17.11 |
| 6,371,988 B1 | 4/2002 | Pafford et al. |
| 6,371,989 B1 | 4/2002 | Chauvin et al. |
| 6,375,681 B1 | 4/2002 | Truscott |
| 6,383,186 B1 | 5/2002 | Michelson |
| 6,387,130 B1 | 5/2002 | Stone et al. |
| 6,395,031 B1 | 5/2002 | Foley et al. |
| 6,398,811 B1 | 6/2002 | McKay |
| 6,413,259 B1 | 7/2002 | Lyons et al. |
| 6,423,063 B1 | 7/2002 | Bonutti |
| 6,432,106 B1 | 8/2002 | Fraser |
| 6,443,987 B1 | 9/2002 | Bryan |
| 6,447,512 B1 | 9/2002 | Landry et al. |
| 6,447,516 B1 | 9/2002 | Bonutti |
| 6,447,546 B1 | 9/2002 | Bramlet et al. |
| 6,451,042 B1 | 9/2002 | Bonutti |
| 6,454,771 B1 | 9/2002 | Michelson |
| 6,458,158 B1 | 10/2002 | Anderson et al. |
| 6,461,359 B1 | 10/2002 | Tribus et al. |
| 6,464,713 B2 | 10/2002 | Bonutti |
| 6,468,289 B1 | 10/2002 | Bonutti |
| 6,468,293 B2 | 10/2002 | Bonutti et al. |
| 6,468,311 B2 | 10/2002 | Boyd et al. |
| 6,471,724 B2 | 10/2002 | Zdeblick et al. |
| 6,475,230 B1 | 11/2002 | Bonutti et al. |
| 6,482,233 B1 | 11/2002 | Aebi et al. |
| 6,500,195 B2 | 12/2002 | Bonutti |
| 6,503,250 B2 | 1/2003 | Paul |
| 6,503,267 B2 | 1/2003 | Bonutti et al. |
| 6,503,277 B2 | 1/2003 | Bonutti |
| 6,511,509 B1 | 1/2003 | Ford et al. |
| 6,524,312 B2 | 2/2003 | Landry et al. |
| 6,543,455 B2 | 4/2003 | Bonutti |
| 6,558,387 B2 | 5/2003 | Errico et al. |
| 6,558,423 B1 | 5/2003 | Michelson |
| 6,558,424 B2 | 5/2003 | Thalgott |
| 6,562,073 B2 | 5/2003 | Foley |
| 6,565,605 B2 | 5/2003 | Goble et al. |
| 6,569,187 B1 | 5/2003 | Bonutti et al. |
| 6,569,201 B2 | 5/2003 | Moumene et al. |
| 6,575,975 B2 | 6/2003 | Brace et al. |
| 6,575,982 B1 | 6/2003 | Bonutti |
| 6,576,017 B2 | 6/2003 | Foley et al. |
| 6,579,290 B1 | 6/2003 | Hardcastle et al. |
| 6,585,750 B2 | 7/2003 | Bonutti et al. |
| 6,592,531 B2 | 7/2003 | Bonutti |
| 6,592,609 B1 | 7/2003 | Bonutti |
| 6,592,624 B1 | 7/2003 | Fraser et al. |
| 6,602,291 B1 | 8/2003 | Ray et al. |
| 6,605,090 B1 | 8/2003 | Trieu et al. |
| 6,607,534 B2 | 8/2003 | Bonutti |
| 6,616,671 B2 | 9/2003 | Landry et al. |
| 6,620,163 B1 | 9/2003 | Michelson |
| 6,620,181 B1 | 9/2003 | Bonutti |
| 6,623,486 B1 | 9/2003 | Weaver et al. |
| 6,629,998 B1 | 10/2003 | Lin |

(56) References Cited

U.S. PATENT DOCUMENTS

| | | |
|---|---|---|
| 6,630,000 B1 | 10/2003 | Bonutti |
| 6,635,073 B2 | 10/2003 | Bonutti |
| 6,638,309 B2 | 10/2003 | Bonutti |
| 6,638,310 B2 | 10/2003 | Lin et al. |
| 6,645,212 B2 | 11/2003 | Goldhahn et al. |
| 6,652,525 B1 | 11/2003 | Assaker et al. |
| 6,652,532 B2 | 11/2003 | Bonutti |
| 6,656,181 B2 | 12/2003 | Dixon et al. |
| 6,679,887 B2 | 1/2004 | Nicholson et al. |
| 6,682,561 B2 | 1/2004 | Songer et al. |
| 6,682,563 B2 | 1/2004 | Scharf |
| 6,695,846 B2 | 2/2004 | Richelsoph et al. |
| 6,695,851 B2 | 2/2004 | Zdeblick et al. |
| 6,702,821 B2 | 3/2004 | Bonutti |
| 6,702,856 B2 | 3/2004 | Bonutti |
| 6,706,067 B2 | 3/2004 | Shimp et al. |
| 6,709,456 B2 | 3/2004 | Langberg et al. |
| 6,712,818 B1 | 3/2004 | Michelson |
| 6,719,803 B2 | 4/2004 | Bonutti |
| 6,730,127 B2 | 5/2004 | Michelson |
| 6,736,850 B2 | 5/2004 | Davis |
| 6,736,853 B2 | 5/2004 | Bonutti |
| 6,743,257 B2 | 6/2004 | Castro |
| 6,761,738 B1 | 7/2004 | Boyd |
| 6,761,739 B2 | 7/2004 | Shepard |
| 6,770,078 B2 | 8/2004 | Bonutti |
| 6,770,096 B2 | 8/2004 | Bolger et al. |
| 6,776,938 B2 | 8/2004 | Bonutti |
| 6,786,909 B1 | 9/2004 | Dransfeld et al. |
| 6,800,092 B1 | 10/2004 | Williams et al. |
| 6,800,093 B2 | 10/2004 | Nicholson et al. |
| 6,805,714 B2 | 10/2004 | Sutcliffe |
| 6,808,537 B2 | 10/2004 | Michelson |
| 6,824,564 B2 | 11/2004 | Crozet |
| 6,833,006 B2 | 12/2004 | Foley et al. |
| 6,835,198 B2 | 12/2004 | Bonutti |
| 6,837,905 B1 | 1/2005 | Lieberman |
| 6,849,093 B2 | 2/2005 | Michelson |
| 6,855,167 B2 | 2/2005 | Shimp et al. |
| 6,855,168 B2 | 2/2005 | Crozet |
| 6,860,885 B2 | 3/2005 | Bonutti |
| 6,860,904 B2 | 3/2005 | Bonutti |
| 6,863,673 B2 | 3/2005 | Gerbec et al. |
| 6,872,915 B2 | 3/2005 | Koga et al. |
| 6,884,242 B2 | 4/2005 | Lehuec et al. |
| 6,890,334 B2 | 5/2005 | Brace et al. |
| 6,896,701 B2 | 5/2005 | Boyd et al. |
| 6,899,735 B2 | 5/2005 | Coates et al. |
| 6,902,578 B1 | 6/2005 | Anderson et al. |
| 6,905,517 B2 | 6/2005 | Bonutti |
| 6,908,466 B1 | 6/2005 | Bonutti et al. |
| 6,916,320 B2 | 7/2005 | Michelson |
| 6,923,756 B2 | 8/2005 | Sudakov et al. |
| 6,932,835 B2 | 8/2005 | Bonutti et al. |
| 6,953,477 B2 | 10/2005 | Berry |
| 6,962,606 B2 | 11/2005 | Michelson |
| 6,964,664 B2 | 11/2005 | Freid et al. |
| 6,964,687 B1 | 11/2005 | Bernard et al. |
| 6,972,019 B2 | 12/2005 | Michelson |
| 6,972,035 B2 | 12/2005 | Michelson |
| 6,974,479 B2 | 12/2005 | Trieu |
| 6,984,234 B2 | 1/2006 | Bray |
| 6,986,788 B2 | 1/2006 | Paul et al. |
| 6,989,029 B2 | 1/2006 | Bonutti |
| 6,990,982 B1 | 1/2006 | Bonutti |
| 7,001,385 B2 | 2/2006 | Bonutti |
| 7,001,432 B2 | 2/2006 | Keller et al. |
| 7,018,412 B2 | 3/2006 | Ferreira et al. |
| 7,018,416 B2 | 3/2006 | Hanson et al. |
| 7,033,394 B2 | 4/2006 | Michelson |
| 7,041,135 B2 | 5/2006 | Michelson |
| 7,044,968 B1 | 5/2006 | Yaccarino et al. |
| 7,044,972 B2 | 5/2006 | Mathys et al. |
| 7,048,755 B2 | 5/2006 | Bonutti et al. |
| 7,048,765 B1 | 5/2006 | Grooms et al. |
| 7,060,097 B2 | 6/2006 | Fraser et al. |
| 7,066,961 B2 | 6/2006 | Michelson |
| 7,070,557 B2 | 7/2006 | Bonutti |
| 7,077,864 B2 | 7/2006 | Byrd et al. |
| 7,087,073 B2 | 8/2006 | Bonutti |
| 7,094,251 B2 | 8/2006 | Bonutti et al. |
| 7,104,996 B2 | 9/2006 | Bonutti |
| 7,112,223 B2 | 9/2006 | Davis |
| 7,119,999 B2 | 9/2006 | Fraser et al. |
| 7,114,500 B2 | 10/2006 | Bonutti |
| 7,128,753 B1 | 10/2006 | Bonutti et al. |
| 7,134,437 B2 | 11/2006 | Bonutti |
| 7,135,024 B2 | 11/2006 | Cook et al. |
| 7,135,043 B2 | 11/2006 | Nakahara et al. |
| 7,137,984 B2 | 11/2006 | Michelson |
| 7,147,652 B2 | 12/2006 | Bonutti et al. |
| 7,147,665 B1 | 12/2006 | Bryan et al. |
| 7,163,561 B2 | 1/2007 | Michelson |
| 7,172,627 B2 | 2/2007 | Fiere et al. |
| 7,172,672 B2 | 2/2007 | Silverbrook |
| 7,208,013 B1 | 4/2007 | Bonutti |
| 7,217,273 B2 | 5/2007 | Bonutti |
| 7,217,290 B2 | 5/2007 | Bonutti |
| 7,226,452 B2 | 6/2007 | Zubok et al. |
| 7,226,482 B2 | 6/2007 | Messerli et al. |
| 7,232,463 B2 | 6/2007 | Falahee |
| 7,232,464 B2 | 6/2007 | Mathieu et al. |
| 7,238,203 B2 | 7/2007 | Bagga et al. |
| 7,255,698 B2 | 8/2007 | Michelson |
| 7,276,082 B2 | 10/2007 | Zdeblick et al. |
| 7,311,719 B2 | 12/2007 | Bonutti |
| 7,320,708 B1 | 1/2008 | Bernstein |
| 7,323,011 B2 | 1/2008 | Shepard et al. |
| 7,329,263 B2 | 2/2008 | Bonutti et al. |
| 7,398,623 B2 | 7/2008 | Martel et al. |
| 7,429,266 B2 | 9/2008 | Bonutti et al. |
| 7,442,209 B2 | 10/2008 | Michelson |
| 7,462,200 B2 | 12/2008 | Bonutti |
| 7,481,831 B2 | 1/2009 | Bonutti |
| 7,485,145 B2 | 2/2009 | Purcell |
| 7,491,237 B2 | 2/2009 | Randall et al. |
| 7,510,557 B1 | 3/2009 | Bonutti |
| 7,534,265 B1 | 5/2009 | Boyd et al. |
| 7,594,932 B2 | 9/2009 | Aferzon et al. |
| 7,601,173 B2 | 10/2009 | Messerli et al. |
| 7,608,107 B2 | 10/2009 | Michelson |
| 7,615,054 B1 | 11/2009 | Bonutti |
| 7,618,456 B2 | 11/2009 | Mathieu et al. |
| 7,621,960 B2 | 11/2009 | Boyd et al. |
| 7,625,380 B2 | 12/2009 | Drewry et al. |
| 7,635,390 B1 | 12/2009 | Bonutti |
| 7,637,951 B2 | 12/2009 | Michelson |
| 7,655,042 B2 | 2/2010 | Foley et al. |
| 7,704,279 B2 | 4/2010 | Moskowitz et al. |
| 7,708,740 B1 | 5/2010 | Bonutti |
| 7,708,741 B1 | 5/2010 | Bonutti |
| 7,727,283 B2 | 6/2010 | Bonutti |
| 7,749,229 B1 | 7/2010 | Bonutti |
| 7,776,067 B2 | 8/2010 | Jackson |
| 7,780,670 B2 | 8/2010 | Bonutti |
| 7,806,896 B1 | 10/2010 | Bonutti |
| 7,806,897 B1 | 10/2010 | Bonutti |
| 7,828,852 B2 | 11/2010 | Bonutti |
| 7,833,271 B2 | 11/2010 | Mitchell et al. |
| 7,837,736 B2 | 11/2010 | Bonutti |
| 7,846,188 B2 | 12/2010 | Moskowitz et al. |
| 7,846,207 B2 | 12/2010 | Lechmann et al. |
| 7,854,750 B2 | 12/2010 | Bonutti et al. |
| 7,862,616 B2 | 1/2011 | Lechmann et al. |
| 7,875,076 B2 | 1/2011 | Mathieu et al. |
| 7,879,072 B2 | 2/2011 | Bonutti et al. |
| 7,892,236 B2 | 2/2011 | Bonutti |
| 7,892,261 B2 | 2/2011 | Bonutti |
| 7,896,880 B2 | 3/2011 | Bonutti |
| 7,931,690 B1 | 4/2011 | Bonutti |
| 7,942,903 B2 | 5/2011 | Moskowitz et al. |
| 7,959,635 B1 | 6/2011 | Bonutti |
| 7,985,255 B2 | 7/2011 | Bray et al. |
| 7,993,403 B2 | 8/2011 | Foley et al. |

(56) References Cited

U.S. PATENT DOCUMENTS

| | | |
|---|---|---|
| 8,062,303 B2 | 11/2011 | Berry et al. |
| 8,100,976 B2 | 1/2012 | Bray et al. |
| 8,105,383 B2 | 1/2012 | Michelson |
| 8,128,669 B2 | 3/2012 | Bonutti |
| 8,128,700 B2 | 3/2012 | Delurio et al. |
| 8,133,229 B1 | 3/2012 | Bonutti |
| 8,162,977 B2 | 4/2012 | Bonutti et al. |
| 8,182,532 B2 | 5/2012 | Anderson et al. |
| 8,187,329 B2 | 5/2012 | Theofilos |
| 8,211,148 B2 | 7/2012 | Zhang et al. |
| 8,273,127 B2 | 9/2012 | Jones et al. |
| 8,308,804 B2 | 11/2012 | Krueger |
| 8,328,872 B2 | 12/2012 | Duffield et al. |
| 8,343,220 B2 | 1/2013 | Michelson |
| 8,343,222 B2 | 1/2013 | Cope |
| 8,353,913 B2 | 1/2013 | Moskowitz et al. |
| 8,382,768 B2 | 2/2013 | Berry et al. |
| 8,425,522 B2 | 4/2013 | Bonutti |
| 8,425,607 B2 | 4/2013 | Waugh et al. |
| 8,444,696 B2 | 5/2013 | Michelson |
| 8,465,546 B2 | 6/2013 | Jodaitis et al. |
| 8,486,066 B2 | 7/2013 | Bonutti |
| 8,540,774 B2 | 9/2013 | Kueenzi et al. |
| 8,545,562 B1* | 10/2013 | Materna ............... A61F 2/442 623/17.11 |
| 8,545,567 B1 | 10/2013 | Krueger |
| 8,613,772 B2 | 12/2013 | Bray et al. |
| 8,623,030 B2 | 1/2014 | Bonutti |
| 8,632,552 B2 | 1/2014 | Bonutti |
| 8,641,726 B2 | 2/2014 | Bonutti |
| 8,641,743 B2 | 2/2014 | Michelson |
| 8,641,768 B2 | 2/2014 | Duffield et al. |
| 8,690,944 B2 | 4/2014 | Bonutti |
| 8,739,797 B2 | 6/2014 | Bonutti |
| 8,747,439 B2 | 6/2014 | Bonutti et al. |
| 8,764,831 B2 | 7/2014 | Lechmann et al. |
| 8,784,495 B2 | 7/2014 | Bonutti |
| 8,795,363 B2 | 8/2014 | Bonutti |
| 8,814,902 B2 | 8/2014 | Bonutti |
| 8,834,490 B2 | 9/2014 | Bonutti |
| 8,840,629 B2 | 9/2014 | Bonutti |
| 8,845,699 B2 | 9/2014 | Bonutti |
| 8,858,557 B2 | 10/2014 | Bonutti |
| 8,900,310 B2* | 12/2014 | Carlson ............... A61F 2/446 623/17.16 |
| 8,956,417 B2 | 2/2015 | Bonutti |
| 9,005,295 B2 | 4/2015 | Kueenzi et al. |
| 9,044,322 B2 | 6/2015 | Bonutti |
| 9,044,341 B2 | 6/2015 | Bonutti |
| 9,050,152 B2 | 6/2015 | Bonutti |
| 9,107,760 B2* | 8/2015 | Walters ............... A61F 2/442 |
| 9,149,365 B2 | 10/2015 | Lawson et al. |
| 9,192,419 B2 | 11/2015 | McDonough et al. |
| 9,198,774 B2* | 12/2015 | Pisharodi ............... A61F 2/447 |
| 9,220,604 B2 | 12/2015 | McDonough et al. |
| 9,241,809 B2 | 1/2016 | McDonough et al. |
| 9,364,340 B2 | 6/2016 | Lawson et al. |
| 9,414,935 B2 | 8/2016 | McDonough et al. |
| 9,463,097 B2 | 10/2016 | Lechmann et al. |
| 9,572,681 B2 | 2/2017 | Mathieu et al. |
| 9,744,049 B2 | 8/2017 | Kueenzi et al. |
| 9,848,992 B2 | 12/2017 | McDonough et al. |
| 9,883,950 B2 | 2/2018 | Bertagnoli et al. |
| 10,010,432 B2 | 7/2018 | Schmura et al. |
| 10,130,492 B2 | 11/2018 | Schmura et al. |
| 10,492,922 B2 | 12/2019 | Mathieu et al. |
| 10,507,117 B2 | 12/2019 | McDonough et al. |
| 10,702,394 B2 | 7/2020 | Schmura et al. |
| 2001/0001129 A1 | 5/2001 | McKay et al. |
| 2001/0005796 A1 | 6/2001 | Zdeblick et al. |
| 2001/0010021 A1 | 7/2001 | Boyd et al. |
| 2001/0016777 A1 | 8/2001 | Biscup |
| 2001/0020186 A1 | 9/2001 | Boyce et al. |
| 2001/0023371 A1 | 9/2001 | Bonutti |
| 2001/0031254 A1 | 10/2001 | Bianchi et al. |
| 2001/0039456 A1 | 11/2001 | Boyer et al. |
| 2001/0041941 A1 | 11/2001 | Boyer et al. |
| 2001/0049560 A1 | 12/2001 | Paul et al. |
| 2002/0004683 A1 | 1/2002 | Michelson |
| 2002/0010511 A1 | 1/2002 | Michelson |
| 2002/0016595 A1 | 2/2002 | Michelson |
| 2002/0022843 A1 | 2/2002 | Michelson |
| 2002/0029055 A1 | 3/2002 | Bonutti |
| 2002/0029084 A1 | 3/2002 | Paul et al. |
| 2002/0040246 A1 | 4/2002 | Bonutti |
| 2002/0049497 A1 | 4/2002 | Mason |
| 2002/0065517 A1 | 5/2002 | Paul |
| 2002/0077702 A1 | 6/2002 | Castro |
| 2002/0082597 A1 | 6/2002 | Fraser |
| 2002/0082603 A1 | 6/2002 | Dixon et al. |
| 2002/0082803 A1 | 6/2002 | Schiffbauer |
| 2002/0091447 A1 | 7/2002 | Shimp et al. |
| 2002/0095155 A1 | 7/2002 | Michelson |
| 2002/0095160 A1 | 7/2002 | Bonutti |
| 2002/0099376 A1 | 7/2002 | Michelson |
| 2002/0099378 A1 | 7/2002 | Michelson |
| 2002/0099444 A1 | 7/2002 | Boyd et al. |
| 2002/0106393 A1 | 8/2002 | Bianchi et al. |
| 2002/0107571 A1 | 8/2002 | Foley |
| 2002/0111680 A1 | 8/2002 | Michelson |
| 2002/0128712 A1 | 9/2002 | Michelson |
| 2002/0128717 A1 | 9/2002 | Alfaro et al. |
| 2002/0147450 A1 | 10/2002 | Lehuec et al. |
| 2002/0169508 A1 | 11/2002 | Songer et al. |
| 2002/0161444 A1 | 12/2002 | Choi |
| 2002/0193880 A1 | 12/2002 | Fraser |
| 2003/0004576 A1 | 1/2003 | Thalgott |
| 2003/0009147 A1 | 1/2003 | Bonutti |
| 2003/0023260 A1 | 1/2003 | Bonutti |
| 2003/0040798 A1* | 2/2003 | Michelson ............... A61F 2/447 623/17.11 |
| 2003/0045939 A1 | 3/2003 | Casutt |
| 2003/0065396 A1 | 4/2003 | Michelson |
| 2003/0078666 A1 | 4/2003 | Ralph et al. |
| 2003/0078668 A1 | 4/2003 | Michelson |
| 2003/0125739 A1 | 7/2003 | Bagga et al. |
| 2003/0135277 A1 | 7/2003 | Bryan et al. |
| 2003/0149484 A1* | 8/2003 | Michelson ............... A61F 2/447 623/17.16 |
| 2003/0153975 A1 | 8/2003 | Byrd et al. |
| 2003/0167092 A1 | 9/2003 | Foley |
| 2003/0181981 A1 | 9/2003 | Lemaire |
| 2003/0187436 A1* | 10/2003 | Bolger ............... A61B 17/7077 606/279 |
| 2003/0195626 A1 | 10/2003 | Huppert |
| 2003/0195632 A1 | 10/2003 | Foley et al. |
| 2003/0199881 A1 | 10/2003 | Bonutti |
| 2003/0199983 A1 | 10/2003 | Michelson |
| 2004/0010287 A1 | 1/2004 | Bonutti |
| 2004/0078078 A1 | 4/2004 | Shepard |
| 2004/0078081 A1 | 4/2004 | Ferree |
| 2004/0092929 A1 | 5/2004 | Zindrick |
| 2004/0093084 A1 | 5/2004 | Michelson |
| 2004/0097794 A1 | 5/2004 | Bonutti |
| 2004/0098016 A1 | 5/2004 | Bonutti |
| 2004/0102848 A1 | 5/2004 | Michelson |
| 2004/0102850 A1 | 5/2004 | Shepard |
| 2004/0126407 A1 | 7/2004 | Falahee |
| 2004/0133278 A1 | 7/2004 | Marino et al. |
| 2004/0138689 A1 | 7/2004 | Bonutti |
| 2004/0138690 A1 | 7/2004 | Bonutti |
| 2004/0143270 A1 | 7/2004 | Zucherman et al. |
| 2004/0143285 A1 | 7/2004 | Bonutti |
| 2004/0172033 A1 | 9/2004 | Bonutti |
| 2004/0176853 A1 | 9/2004 | Sennett et al. |
| 2004/0193181 A1 | 9/2004 | Bonutti |
| 2004/0193269 A1 | 9/2004 | Fraser et al. |
| 2004/0199254 A1 | 10/2004 | Louis et al. |
| 2004/0210219 A1 | 10/2004 | Bray |
| 2004/0210310 A1 | 10/2004 | Trieu |
| 2004/0210314 A1 | 10/2004 | Michelson |
| 2004/0220668 A1 | 11/2004 | Eisermann et al. |
| 2004/0230223 A1 | 11/2004 | Bonutti et al. |
| 2004/0249377 A1 | 12/2004 | Kaes et al. |

(56) References Cited

U.S. PATENT DOCUMENTS

| | | |
|---|---|---|
| 2004/0254644 A1 | 12/2004 | Taylor |
| 2004/0260427 A1 | 12/2004 | Wimsatt |
| 2005/0015149 A1 | 1/2005 | Michelson |
| 2005/0021042 A1 | 1/2005 | Marnay et al. |
| 2005/0021143 A1 | 1/2005 | Keller |
| 2005/0033433 A1 | 2/2005 | Michelson |
| 2005/0049593 A1 | 3/2005 | Duong et al. |
| 2005/0049595 A1 | 3/2005 | Suh et al. |
| 2005/0065605 A1 | 3/2005 | Jackson |
| 2005/0065607 A1 | 3/2005 | Gross |
| 2005/0065608 A1 | 3/2005 | Michelson |
| 2005/0071008 A1 | 3/2005 | Kirschman |
| 2005/0085913 A1 | 4/2005 | Fraser et al. |
| 2005/0101960 A1 | 5/2005 | Fiere et al. |
| 2005/0113918 A1 | 5/2005 | Messerli et al. |
| 2005/0113920 A1 | 5/2005 | Foley et al. |
| 2005/0125029 A1 | 6/2005 | Bernard et al. |
| 2005/0149193 A1 | 7/2005 | Zucherman et al. |
| 2005/0154391 A1 | 7/2005 | Doherty et al. |
| 2005/0159813 A1 | 7/2005 | Molz, IV |
| 2005/0159818 A1 | 7/2005 | Blain |
| 2005/0159819 A1 | 7/2005 | McCormack et al. |
| 2005/0171606 A1 | 8/2005 | Michelson |
| 2005/0171607 A1 | 8/2005 | Michelson |
| 2005/0177236 A1 | 8/2005 | Mathieu et al. |
| 2005/0216059 A1 | 9/2005 | Bonutti et al. |
| 2005/0222683 A1 | 10/2005 | Berry |
| 2005/0240267 A1 | 10/2005 | Randall et al. |
| 2005/0240271 A1 | 10/2005 | Zubok et al. |
| 2005/0261767 A1 | 11/2005 | Anderson et al. |
| 2005/0267534 A1 | 12/2005 | Bonutti et al. |
| 2005/0283236 A1* | 12/2005 | Razian .................. A61F 2/447 623/17.11 |
| 2006/0020342 A1 | 1/2006 | Ferree et al. |
| 2006/0030851 A1 | 2/2006 | Bray et al. |
| 2006/0079901 A1 | 4/2006 | Ryan et al. |
| 2006/0079961 A1 | 4/2006 | Michelson |
| 2006/0085071 A1 | 4/2006 | Lechmann et al. |
| 2006/0089717 A1 | 4/2006 | Krishna et al. |
| 2006/0129240 A1 | 6/2006 | Lessar et al. |
| 2006/0136063 A1 | 6/2006 | Zeegers |
| 2006/0142765 A9 | 6/2006 | Dixon et al. |
| 2006/0167495 A1 | 7/2006 | Bonutti et al. |
| 2006/0195189 A1 | 8/2006 | Link et al. |
| 2006/0195193 A1 | 8/2006 | Bloemer |
| 2006/0206208 A1 | 9/2006 | Michelson |
| 2006/0229725 A1 | 10/2006 | Lechmann et al. |
| 2006/0235470 A1 | 10/2006 | Bonutti et al. |
| 2006/0265009 A1 | 11/2006 | Bonutti |
| 2007/0088358 A1 | 4/2007 | Yuan et al. |
| 2007/0088441 A1 | 4/2007 | Duggal et al. |
| 2007/0093819 A1 | 4/2007 | Albert |
| 2007/0106384 A1 | 5/2007 | Bray et al. |
| 2007/0118125 A1 | 5/2007 | Orbay et al. |
| 2007/0123987 A1 | 5/2007 | Bernstein |
| 2007/0162130 A1 | 7/2007 | Rashbaum et al. |
| 2007/0168032 A1 | 7/2007 | Muhanna et al. |
| 2007/0177236 A1 | 8/2007 | Kijima et al. |
| 2007/0208378 A1 | 9/2007 | Bonutti et al. |
| 2007/0219365 A1 | 9/2007 | Joyce et al. |
| 2007/0219635 A1 | 9/2007 | Mathieu et al. |
| 2007/0225806 A1 | 9/2007 | Squires et al. |
| 2007/0225812 A1 | 9/2007 | Gill |
| 2007/0250167 A1 | 10/2007 | Bray et al. |
| 2007/0270961 A1 | 11/2007 | Ferguson |
| 2008/0033440 A1 | 2/2008 | Moskowitz et al. |
| 2008/0039873 A1 | 2/2008 | Bonutti et al. |
| 2008/0047567 A1 | 2/2008 | Bonutti |
| 2008/0051890 A1 | 2/2008 | Waugh et al. |
| 2008/0058822 A1 | 3/2008 | Bonutti |
| 2008/0065140 A1 | 3/2008 | Bonutti |
| 2008/0082169 A1 | 4/2008 | Gittings et al. |
| 2008/0103519 A1 | 5/2008 | Bonutti |
| 2008/0108916 A1 | 5/2008 | Bonutti et al. |
| 2008/0114399 A1 | 5/2008 | Bonutti |
| 2008/0119933 A1 | 5/2008 | Aebi et al. |
| 2008/0132949 A1 | 6/2008 | Aferzon et al. |
| 2008/0133013 A1 | 6/2008 | Duggal et al. |
| 2008/0140116 A1 | 6/2008 | Bonutti |
| 2008/0140117 A1 | 6/2008 | Bonutti et al. |
| 2008/0161925 A1 | 7/2008 | Brittan et al. |
| 2008/0177307 A1 | 7/2008 | Moskowitz et al. |
| 2008/0188940 A1 | 8/2008 | Cohen et al. |
| 2008/0200984 A1 | 8/2008 | Jodaitis et al. |
| 2008/0206297 A1 | 8/2008 | Roeder et al. |
| 2008/0234822 A1 | 9/2008 | Govil et al. |
| 2008/0249569 A1 | 10/2008 | Waugh et al. |
| 2008/0249575 A1 | 10/2008 | Waugh et al. |
| 2008/0249622 A1 | 10/2008 | Gray |
| 2008/0249625 A1 | 10/2008 | Waugh et al. |
| 2008/0269806 A1 | 10/2008 | Zhang et al. |
| 2008/0275455 A1 | 11/2008 | Berry et al. |
| 2008/0281425 A1 | 11/2008 | Thalgott et al. |
| 2008/0306596 A1 | 12/2008 | Jones et al. |
| 2008/0312742 A1 | 12/2008 | Abernathie |
| 2009/0076608 A1 | 3/2009 | Gordon et al. |
| 2009/0088849 A1 | 4/2009 | Armstrong et al. |
| 2009/0099601 A1* | 4/2009 | Aferzon .................. A61F 2/4611 623/17.11 |
| 2009/0099661 A1 | 4/2009 | Bhattacharya et al. |
| 2009/0105830 A1 | 4/2009 | Jones et al. |
| 2009/0132051 A1 | 5/2009 | Moskowitz et al. |
| 2009/0192613 A1 | 7/2009 | Wing et al. |
| 2009/0210062 A1 | 8/2009 | Thalgott et al. |
| 2009/0210064 A1 | 8/2009 | Lechmann et al. |
| 2009/0234455 A1 | 9/2009 | Moskowitz et al. |
| 2009/0326580 A1 | 12/2009 | Anderson et al. |
| 2010/0016901 A1 | 1/2010 | Robinson |
| 2010/0125334 A1 | 5/2010 | Krueger |
| 2010/0145459 A1 | 6/2010 | McDonough et al. |
| 2010/0145460 A1 | 6/2010 | McDonough et al. |
| 2010/0305704 A1 | 12/2010 | Messerli et al. |
| 2010/0312346 A1 | 12/2010 | Kueenzi et al. |
| 2011/0087327 A1 | 4/2011 | Lechmann et al. |
| 2011/0118843 A1 | 5/2011 | Mathieu et al. |
| 2011/0137417 A1 | 6/2011 | Lee |
| 2011/0166660 A1 | 7/2011 | Laurence |
| 2011/0230971 A1 | 9/2011 | Donner et al. |
| 2011/0238184 A1 | 9/2011 | Zdeblick et al. |
| 2011/0295371 A1 | 12/2011 | Moskowitz et al. |
| 2012/0010623 A1 | 1/2012 | Bonutti |
| 2012/0101581 A1 | 4/2012 | Mathieu et al. |
| 2012/0109309 A1 | 5/2012 | Mathieu et al. |
| 2012/0109310 A1 | 5/2012 | Mathieu et al. |
| 2012/0109311 A1 | 5/2012 | Mathieu et al. |
| 2012/0109312 A1 | 5/2012 | Mathieu et al. |
| 2012/0109313 A1 | 5/2012 | Mathieu et al. |
| 2012/0179259 A1 | 7/2012 | McDonough et al. |
| 2012/0197401 A1 | 8/2012 | Duncan et al. |
| 2012/0215226 A1 | 8/2012 | Bonutti |
| 2012/0215233 A1 | 8/2012 | Bonutti et al. |
| 2012/0221017 A1 | 8/2012 | Bonutti |
| 2012/0323330 A1 | 12/2012 | Kueenzi et al. |
| 2013/0073046 A1 | 3/2013 | Zaveloff et al. |
| 2013/0073047 A1 | 3/2013 | Laskowitz et al. |
| 2013/0166032 A1 | 6/2013 | McDonough et al. |
| 2013/0173013 A1 | 7/2013 | Anderson et al. |
| 2013/0226185 A1 | 8/2013 | Bonutti |
| 2013/0237989 A1 | 9/2013 | Bonutti |
| 2013/0268008 A1 | 10/2013 | McDonough et al. |
| 2013/0289729 A1 | 10/2013 | Bonutti |
| 2014/0018854 A1 | 1/2014 | Bonutti et al. |
| 2014/0025110 A1 | 1/2014 | Bonutti et al. |
| 2014/0025111 A1 | 1/2014 | Bonutti et al. |
| 2014/0025112 A1 | 1/2014 | Bonutti |
| 2014/0025168 A1 | 1/2014 | Klimek et al. |
| 2014/0081406 A1 | 3/2014 | Kellar et al. |
| 2014/0100663 A1 | 4/2014 | Messerli et al. |
| 2014/0121777 A1 | 5/2014 | Rosen et al. |
| 2014/0180422 A1 | 6/2014 | Klimek et al. |
| 2014/0214166 A1 | 7/2014 | Theofilos |
| 2014/0228963 A1 | 8/2014 | Bonutti |
| 2014/0243985 A1 | 8/2014 | Lechmann et al. |
| 2014/0257380 A1 | 9/2014 | Bonutti |

(56) References Cited

U.S. PATENT DOCUMENTS

| | | |
|---|---|---|
| 2014/0257487 A1 | 9/2014 | Lawson et al. |
| 2014/0277456 A1 | 9/2014 | Kirschman |
| 2014/0309560 A1 | 10/2014 | Bonutti |
| 2014/0336770 A1 | 11/2014 | Petersheim et al. |
| 2014/0343573 A1 | 11/2014 | Bonutti |
| 2014/0371859 A1 | 12/2014 | Petersheim et al. |
| 2015/0257893 A1 | 9/2015 | Mazzuca et al. |
| 2015/0320571 A1 | 11/2015 | Lechmann et al. |
| 2016/0113774 A1 | 4/2016 | Schmura et al. |
| 2020/0281740 A1 | 9/2020 | Schmura et al. |

FOREIGN PATENT DOCUMENTS

| | | |
|---|---|---|
| CA | 2317791 A1 | 8/1999 |
| CN | 1383790 A | 12/2002 |
| CN | 1620271 A | 5/2005 |
| CN | 1701772 A | 11/2005 |
| CN | 1901853 A | 1/2007 |
| DE | 2821678 A | 11/1979 |
| DE | 3042003 A1 | 7/1982 |
| DE | 3933459 A1 | 4/1991 |
| DE | 4242889 A1 | 6/1994 |
| DE | 4409392 A1 | 9/1995 |
| DE | 4423257 A1 | 1/1996 |
| DE | 19504867 C1 | 2/1996 |
| DE | 29913200 U1 | 9/1999 |
| DE | 202004020209 U1 | 5/2006 |
| EP | 0179695 A1 | 4/1986 |
| EP | 0298233 A1 | 1/1989 |
| EP | 0302719 A1 | 2/1989 |
| EP | 0505634 A1 | 9/1992 |
| EP | 0577178 A1 | 1/1994 |
| EP | 0639351 A2 | 2/1995 |
| EP | 0425542 B1 | 3/1995 |
| EP | 0504346 B1 | 5/1995 |
| EP | 0517030 B1 | 9/1996 |
| EP | 0897697 A1 | 2/1999 |
| EP | 0605799 B1 | 4/1999 |
| EP | 0641547 B1 | 5/1999 |
| EP | 0966930 A1 | 12/1999 |
| EP | 0968692 A1 | 1/2000 |
| EP | 0974319 A2 | 1/2000 |
| EP | 1124512 A1 | 8/2001 |
| EP | 1194087 A1 | 4/2002 |
| EP | 1393689 A2 | 3/2004 |
| EP | 1402836 A2 | 3/2004 |
| EP | 1033941 B1 | 8/2004 |
| EP | 0906065 B1 | 9/2004 |
| EP | 1051133 B1 | 10/2004 |
| EP | 1103236 B1 | 8/2006 |
| EP | 1459711 B1 | 7/2007 |
| EP | 1847240 A1 | 10/2007 |
| FR | 2552659 A3 | 4/1985 |
| FR | 2697996 A1 | 5/1994 |
| FR | 2700947 A1 | 8/1994 |
| FR | 2703580 A1 | 10/1994 |
| FR | 2727003 A1 | 5/1996 |
| FR | 2747034 A1 | 10/1997 |
| FR | 2753368 A1 | 3/1998 |
| GB | 0157668 A | 1/1921 |
| GB | 0265592 A | 8/1927 |
| GB | 2148122 A | 5/1985 |
| GB | 2207607 A | 2/1989 |
| GB | 2239482 A | 7/1991 |
| GB | 2266246 A | 10/1993 |
| JP | 03-505416 A | 11/1991 |
| JP | 09-280219 A | 10/1997 |
| JP | 2006-513752 A | 4/2006 |
| MX | 9601079 A | 7/1997 |
| RU | 2229271 C1 | 5/2004 |
| RU | 2244527 C2 | 1/2005 |
| RU | 2307625 C1 | 10/2007 |
| SU | 1465040 A1 | 3/1989 |
| WO | 88/03417 A1 | 5/1988 |
| WO | 88/10100 A1 | 12/1988 |
| WO | 89/09035 A1 | 10/1989 |
| WO | 90/00037 A1 | 1/1990 |
| WO | 92/01428 A1 | 2/1992 |
| WO | 92/06005 A1 | 4/1992 |
| WO | 93/01771 A1 | 2/1993 |
| WO | 95/08964 A2 | 4/1995 |
| WO | 95/15133 A1 | 6/1995 |
| WO | 95/20370 A1 | 8/1995 |
| WO | 95/21053 A1 | 8/1995 |
| WO | 95/26164 A1 | 10/1995 |
| WO | 96/39988 A2 | 12/1996 |
| WO | 96/40015 A1 | 12/1996 |
| WO | 97/20526 A1 | 6/1997 |
| WO | 97/23175 A1 | 7/1997 |
| WO | 97/25941 A1 | 7/1997 |
| WO | 97/25945 A1 | 7/1997 |
| WO | 97/37620 A1 | 10/1997 |
| WO | 97/39693 A1 | 10/1997 |
| WO | 98/17208 A2 | 4/1998 |
| WO | 98/17209 A2 | 4/1998 |
| WO | 98/55052 A1 | 12/1998 |
| WO | 98/56319 A1 | 12/1998 |
| WO | 98/56433 A1 | 12/1998 |
| WO | 99/09896 A1 | 3/1999 |
| WO | 99/09903 A1 | 3/1999 |
| WO | 99/27864 A2 | 6/1999 |
| WO | 99/29271 A1 | 6/1999 |
| WO | 99/32055 A1 | 7/1999 |
| WO | 99/38461 A2 | 8/1999 |
| WO | 99/38463 A2 | 8/1999 |
| WO | 99/56675 A1 | 11/1999 |
| WO | 99/63914 A1 | 12/1999 |
| WO | 00/07527 A1 | 2/2000 |
| WO | 00/07528 A1 | 2/2000 |
| WO | 00/25706 | 5/2000 |
| WO | 00/30568 A1 | 6/2000 |
| WO | 00/40177 A1 | 7/2000 |
| WO | 00/41654 A2 | 7/2000 |
| WO | 00/59412 A1 | 10/2000 |
| WO | 00/66044 A1 | 11/2000 |
| WO | 00/66045 A1 | 11/2000 |
| WO | 00/74607 A1 | 12/2000 |
| WO | 01/03615 A1 | 1/2001 |
| WO | 01/08611 A1 | 2/2001 |
| WO | 01/56497 A2 | 8/2001 |
| WO | 01/62190 A1 | 8/2001 |
| WO | 01/80785 A1 | 11/2001 |
| WO | 01/93742 A2 | 12/2001 |
| WO | 01/95837 A1 | 12/2001 |
| WO | 2004/000177 A1 | 12/2003 |
| WO | 2004/069106 A1 | 8/2004 |
| WO | 2005/007040 A1 | 1/2005 |
| WO | 2005/020861 A1 | 3/2005 |
| WO | 2006/138500 A2 | 12/2006 |
| WO | 07/98288 A2 | 8/2007 |
| WO | 2008/014258 A2 | 1/2008 |
| WO | 2008/082473 A1 | 7/2008 |
| WO | 2008/102174 A2 | 8/2008 |
| WO | 2008/124355 A1 | 10/2008 |
| WO | 2008/154326 A1 | 12/2008 |
| WO | 2009/064644 A1 | 5/2009 |
| WO | 2009/158319 A1 | 12/2009 |
| WO | 2010/054181 A1 | 5/2010 |
| WO | 2010/054208 A1 | 5/2010 |
| WO | 2012/088238 A2 | 6/2012 |

OTHER PUBLICATIONS

U.S. Appl. No. 11/199,599: Interview Summary included Draft Amendments, dated Sep. 24, 2009, 16 pages.

U.S. Appl. No. 11/199,599: Non-Final Rejection, dated Apr. 1, 2009, 20 pages.

U.S. Appl. No. 11/199,599: Preliminary Amendment, dated Jan. 9, 2008, 11 pages.

U.S. Provisional Application Filed on Dec. 19, 1997 by David J. Urbahns et al., entitled "Insertion Instruments and Method for Delivering a Vertebral Body Spacer", U.S. Appl. No. 60/068,205.

(56) References Cited

OTHER PUBLICATIONS

U.S Provisional Application Filed on Jan. 15, 1998 by David J. Urbahns et al., entitled "Insertion Instruments and Method for Delivering a Vertebral Body Spacer", U.S. Appl. No. 60/071,527.
U.S. Provisional Application Filed on Nov. 16, 2007 by Thomas Kueenzi et. al., entitled "Low profile intervertebral implant", U.S. Appl. No. 60/988,661.
U.S. Provisional Application Filed on Sep. 16, 2011 by Jillian Zaveloff et. al., entitled "Multi-Piece Intervertebral Implants", U.S. Appl. No. 61/535,726.
Verbiest H., La Chirurgie Anterieure et Laterale du Rachis Cervical,16(S2) Neurochirurgie 1-212; 1970 (w/Translation).
Wang, Determination of Cortical Bone Porosity and Pore Size Distribution using a Low Field Pulsed NMR Approach, J. Orthop Res., Mar; 21(2):312-9 Mar. 2003.
Wang, Increased Fusion Rates with Cervical Plating for Two-Level Anterior Cervical Discectomy and Fusion, 25(1) Spine 41-45, Jan. 2000.
Watters, Anterior Cervical Discectomy with and without Fusion, 19(20) Spine 2343-2347 Oct. 1994.
Weiner, Spinde Update Lumbar Interbody Cages, 23(5) Spine, 634-640, Mar. 1998.
White, Relief of Pain by Anterior Cervical-Spine Fusion for Spondylosis, 55-A(3) J. Bone Joint Surg. 525-534, Apr. 1973.
Whitesides, Lateral Approach to the Upper Cervical Spine for Anterior Fusion, vol. 59, South Med J, 879-883, Aug. 1966.
Wilson, Anterior Cervical Discetomy without Bone Graft, 47(4) J. Neurosurg. 551-555, Oct. 1977.
Written Opinion, dated Mar. 20, 2009, for PCT International Application No. PCT/US08/82473, filed Nov. 5, 2008.
Younger, Morbidity at Bone Graft Donor Sites, 3(3) J. Orth. Trauma, 192-195, 1989.
Kozak, Anterior Lumbar Fusion Options, No. 300, Clin. Orth. Rel. Res., 45-51, 1994.
Kroppenstedt, Radiological Comparison of Instrumented Posterior Lumbar Interbody Fusion with One or Two Closed-3ox Plasmapore Coated Titanium Cages, 33(19) Spine, 2083-2088, Sep. 2008.
Lund, Interbody Cage Stabilisation in the Lumbar Spine, 80-B(2) J Bone Joint Surg., 351-359, Mar. 1998.
Lyu, Degradability of Polymers for Implantable Biomedical Devices, 10, Int. J. Mol. Sci., 4033-4065, 2009.
Malca, Cervical Interbody Xenografl with Plate Fixation, 21 (6) Spine, 685-690, Mar. 1996.
Marcolongo et al., "Trends in Materials for Spine Surgery", Comprehensive Biomaterials, Biomaterials and Clinical Use, 6.610, Oct. 2011, 21 pages.
McAfee, Minimally Invasive Anterior Retroperitoneal Approach to the Lumbar Spine, 21(13) Spine, 1476-1484, 1998.
Memorandum Opinion, United States District Court District of Delaware, Civil Action No. 1:11-cv-00652-LPS, May 7, 2013, 33 pages.
Nasca, Newer Lumbar Interbody Fusion Techniques, 22(2) J. Surg. Ortho. Advances, 113-117, 2013.
Order, United States District Court District of Delaware, Civil Action No. 1:11-cv-00652-LPS, May 15, 2013, 4 pages.
Order, United States District Court District of Delaware, Civil Action No. 1:11-cv-00652-LPS, May 7, 2013, 7 pages.
Parlov et al., "Anterior Lumbar Interbody Fusion with Threaded Fusion Cages and Autologous Grafts", Eur. Spine J., 1000, 9, 224-229.
PCB Evolution Surgical Technique Guide 2010.
PCT International Application No. PCT/US2009/063529: International Search Report and Written Opinion dated Apr. 14, 2010, 19 pages.
Plaintiffs' Responses and Objections to Defendant Globus Medical, Inc.'s First Set of Interrogatories (Nos. 1-11), United States District Court for the District of Delaware, Civil Action No. 1:11-cv-00652-LPS, Nov. 14, 2011, 18 pages.
Plaintiffs' Supplemental Responses and Objections to Defendant Globus Medical Inc. 's Interrogatories Nos. 6-10 and Second Supplemental Responses and Objections to Interrogatory No. 5, United States District Court for the District of Delaware, Civil Action No. 11-cv-652-LPS, Sep. 1, 2012, 12 pages.
Polysciences Inc. Info Sheet 2012.
Porex Website, http://www.porex.com/technologies/materials/porous-plastics, Porous Plastic Materials, accessed Aug. 21, 2015, 2 pages.
Redacted version of "Defendant Globus Medical, Inc.'s Answering Brief in Opposition to Plaintiffs Motion for Summary Judgment of No Anticipation by the Kozak and Michelson References", Mar. 12, 2013, 233 pages.
Redacted version of "Opening Brief in Support of Plaintiffs' Motion for Summary Judgment of No Anticipation by the Kozak and Michelson References", United States District Court District of Delaware, Civil Action No. 1:11-cv-00652-LPS, Feb. 13, 2013, 66 pages.
Redacted version of "Plaintiff's Reply Brief in Support of Plaintiff's Motion for Summary Judgment of No Anticipation by the Kozak and Michelson References", Mar. 21, 2013, 11 pages.
Reply Report of Dr. Domagoj Carie Regarding the Invalidity of U.S. Pat. No. 7,846,207, U.S. Pat. No. 7,862,616 and U.S. Pat. No. 7,875,076, In the United States District Court for the District of Delaware,Civil Action No. 1 :11-cv-00652-LPS, Jan. 4, 2013, 81 pages.
Russian Patent Application No. 2011-1122797: Decision to Grant dated Oct. 9, 2013, 20 page.
Samandouras, A New Anterior Cervical Instrumentation System Combinin an Intradiscal Cage with an Integrated plate, 26(10) Spine, 1188-1192, 2001.
Schleicher et al., "Biomechanical Comparison of Two Different Concepts for Stand alone anterior lumbar interbody fusion", Eur Spine J., Sep. 2008, 17, 1757-1765.
Scholz et al., "A New Stand-Alone Cervical Anterior Interbody Fusion Device", Spine, Jan. 2009, 34(2), 6 pages.
Second Expert Report of Wilson C. Hayes, Ph.D., United States District Court for the District of Delaware, Civil Action No. 1:11-cv-00652-LPS, Dec. 14, 2012, 22 pages.
Sonntag, Controversy in Spine Care, Is Fusion Necessary Arter Anterior Cervical Discectomy 21(9) Spine, 1111-1113, May 1996.
Spruit et al., "The in Vitro Stabilizing Effect of Polyether-etherketone Cages Versus a Titanium Cage of similar design for anterior lumbar interbody fusion", Eur. Spine J., Aug. 2005, 14 752-758.
Synthes History and Evolution of LBIF Brochure; Nov. 2015, 30 pages.
Synthes Spine Cervical Stand-Alone Devices Presentation Brochure; 2010, 40 pages.
Synthes Spine, "CorticoCancellous ACF Spacer. An allograft space or anterior fusion of the cervical spine," brochure, Musculoskeletal Transplant Foundationm, 2003, 6 pages.
Synthes Spine, "SynFix-LR System, Instruments and Implants for Stand-Alone Anterior Lumbar Interbody Fusion(ALIF)", Technique Guide dated 2008, pp. 2-40, Published by Synthes Spine (USA).
Synthes Spine, "Zero-P Instruments and Implants. Zero-Profile Anterior Cervical Interbody Fusion (ACIF) device", Technique Guide dated 2008, pp. 2-32, Published by Synthes Spine (USA).
Takahama, A New Improved Biodegradable Tracheal Prosthesis Using Hydroxy Apatite and Barbon Fiber 35(3) ASAIO Trans, 291-293, Jul.-Sep. 1989.
Tamariz, Biodegradation of Medical Purpose Polymeric Materials and Their Impacton Biocompatibility, Chapter 1, Intech-bio degradation Life of Science, 2013; 28 pages.
Tan, A Modified Technique of Anterior Lumbar Fusion with Femoral Cortical Allograft, 5(3) J. Ortho. Surg. Tech., 83-93, 1990.
Trial Transcript, United States District Court District of Delaware, Civil Action No. 1:11-cv-00652-LPS, Jun. 10, 2013, 114 pages.
Trial Transcript, United States District Court District of Delaware, Civil Action No. 1:11-cv-00652-LPS, Jun. 11, 2013, 98 pages.
Trial Transcript, United States District Court District of Delaware, Civil Action No. 1:11-cv-00652-LPS, Jun. 12, 2013, 75 pages.
Trial Transcript, United States District Court District of Delaware, Civil Action No. 1:11-cv-00652-LPS, Jun. 13, 2013, 94 pages.
Trial Transcript, United States District Court District of Delaware, Civil Action No. 1:11-cv-00652-LPS, Jun. 14, 2013, 26 pages.

(56) References Cited

OTHER PUBLICATIONS

Trial Transcript, United States District Court District of Delaware, Civil Action No. 1:11-cv-00652-LPS, Jun. 3, 2013, 98 pages.
Trial Transcript, United States District Court District of Delaware, Civil Action No. 1:11-cv-00652-LPS, Jun. 4, 2013, 110 pages.
Trial Transcript, United States District Court District of Delaware, Civil Action No. 1:11-cv-00652-LPS, Jun. 5, 2013, 99 pages.
Trial Transcript, United States District Court District of Delaware, Civil Action No. 1:11-cv-00652-LPS, Jun. 6, 2013, 80 pages.
Trial Transcript, United States District Court District of Delaware, Civil Action No. 1:11-cv-00652-LPS, Jun. 7, 2013, 97 pages.
U.S. Appl. No. 11/199,599: Amendment/Request for Reconsideration after Non-Final Rejection, dated Sep. 29, 2009, 30 pages.
U.S. Appl. No. 11/199,599: Appeal Brief, dated Apr. 15, 2010, 51 pages.
AcroMed Carbon Fiber Interbody Fusion Devices; Jan. 1998, 8 pages.
Al-Sanabani, Application of Calcium Phosphate Materials in Dentistry, vol. 2013, Int. J. Biomaterials, 1-12, 2013.
Appendix 1 to Joint Claim Construction Brief,A—Synthes' Exhibits A-9, In the United States District Court for the District of Delaware Civil Action No. 1 :11-cv-00652-LPS, Jun. 8, 2012,192 pages.
Appendix 2 to Joint Claim Construction Brief, Globus' Exhibits A-F, In the United States District Court for the District of Delaware Civil Action No. 1 :11-cv-00652-LPS, Jun. 8, 2012, 146 pages.
Appendix 3 to Joint Claim Construction Brief, Exhibits A-C, In the United States District Court for the District of Delaware Civil Action No. 1: 11-cv-00652-LPS, Jun. 8, 2012, 38 pages.
Bailey, Stabilzation of the Cervical Spine by Anterior Fusion, 42-A(4), J. Bone Joint Surg., 565-594, Jun. 1960.
Banward, Iliac Crest Bone Graft Harvest Donor Site Morbidity, 20 (9) Spine 1055-1060, May 1995.
Benezech, L'arthrodese Cervicale Par Voie Anterieure a L'Aide de Plaque-Cage P.C.B., 9(1) Rach is 1, 47, 1997 (w/Translation).
Brantigan 1/F Cage for PLIF Surgical Technique Guide; Apr. 1991, 22 pages.
Brantigan, A Carbon Fiber Implant to Aid Interbody Lumbar Fusion, 16(6S) Spine S277-S282, Jul. 1991.
Brantigan, Compression Strength of Donor Bone for Posterior Lumbar Interbody Fusion, 18(9) Spine 1213-1221, 1993.
Brantigan, Interbody Lumbar Fusion Using a Carbon Fiber Cage Implant Versus Allograft Bone, 19(13) Spine 1436-1444, 1994.
Brantigan, Intervertebral Fusion,Chapter 27, posterior Lumbar Interbody Fusion Using the Lumber Interbody Fusion Cage , 437-466, Jul. 2006.
Bray, "InterPlate Spine Fusion Device: Subsidence Control Without Stress Shielding", Orthopaedic Product News, Sep./Oct. 2006, pp. 22-25.
Bray, InterPlate Vertebral Body Replacement; website accessed May 4, 2017; http://rsbspine.com/Products.aspx, 2 pages.
Carbon Fiber Composite Ramps for Lumbar Interbody Fusion; Apr. 1997, 2 pages.
Chadwick et al., "Radiolucent Structural Materials For Medical Application", vww.mddionline.com/print/238 Jun. 2001, accessed Jul. 31, 2012, 9 pages.
Cloward, Gas-Sterilized Cadaver Bone Grafts for Spinal Fusion Operations, 5(1) Spine 4-10 Jan./Feb. 1980.
Cloward, The Anterior Approach for Removal of Ruptured Cervical Disks, vol. i 5, J. Neuro. 602-617, 1958.
Dabrowski, Highly Porous Titanium Scaffolds for Orthopaedic Applications, J. Biomed Mater. Res. B. Appl. Biomat. Oct.;95(1):53-61, 2010.
Delecrin, Morbidite du Prelevement de Greffons osseuz au Niveau des Cretes Iliaques dans la Chirurgie Du Rachis; Justification du recours aux substituts osseuz, 13(3) Rachis 167-174, 2001 (w/Translation).
DePuy Motech Surgical Titanium Mesh Brochure; 1998, 13 pages.
Dereymaeker, Nouvelle Cure neuro-Chirurgicale de discopathies Cervicales, 2 Neurochimrgie 226-234; 1956 (w/Translation).

Dickman, Internal Fixation and Fusion of the Lumbar Spine Using Threaded Interbody Cages, 13(3) Barrow Quarterly (1997); http://www.thebarrow.org/Education_And_Resources/Barrow_Quarterly/204837.
Enker, Interbody Fusion and Instrumentation, No. 300 Clin. Orth. Rel. Res. 90-101, Mar. 1994.
Expert Report of Dr. Domagoj Carie Regarding the Invalidity of U.S. Pat. No. 7,846,207, U.S. Pat. No. 7,862,616 and U.S. Pat. No. 7,875,076, In the United States District Court for the District of Delaware, Civil Action No. 1:11-cv-00652-LPS, Nov. 5, 2012, 149 pages.
Expert Report of John F. Hall, M.D., United States District Court for the District of Delaware,Civil Action No. 1:11-cv-00652-LPS, Dec. 14, 2012, 27 paqes.
Expert Report of Paul Ducheyne, PH.D. Concerning Patent Validity, United States District Court District of Delaware, Civil Action No. 1 :11-cv-00652-LPS,Dec. 13, 2012, 155pages.
Expert Report of Richard J. Gering, Ph.D., CLP In the United States District Court for the District of Delaware, Civil Action No. 1:11-cv-00652-LPS, Dec. 14, 2012, 39 pages.
Fassio, Use of Cervical Plate-Cage PCB and Results for Anterior Fusion in Cervical Disk Syndrome, 15(6) Rachis 355-361, Dec. 2003 Translation.
Fowler, Complications Associated with Harvesting Autogenous Iliac Bone Graft, 24(12) Am. J. Ortho. 895-904, Dec. 1995.
Fuentes, Les Complications de la Chirurgie Par Voie Anterieure du Rachis Cervical, 8(1) Rachis 3-14, 1996 (w/translalion).
Germay, Resultats Cliniques de Ceramiques D'hydroxyapatite dans les arthrodeses Inter-somatiques du Rachis Dervical Par Voie Anterieure. Etude Retrospective a Propose de 67 cas. 13(3), Rachis 189-195, 2001 (w/Translation).
Graham, Lateral Extracavitary Approach to the Thoracic and Thoracolumbar Spine, 20(7) Orthopedics, 605-610, Jul. 1997.
Gunatillake, Biodegradable Synthetic Polymers for Tissue Engineering, vol. 5, Eur. Cells Materials, 1-16, 2003.
Huttner, Spinal Stenosis & Posterior Lumbar Interbody Fusion, No. 193, Clinical Ortho Rel. Res. 103-114, Mar. 1985.
International Patent Application No. PCT/CH2003/00089, International Search Report, dated Dec. 3, 2003, 3 pages.
International Patent Application No. PCT /US2011/066421; International Search Report and Written Opinion dated Jun. 14, 2012, 31 pages.
International Search Report, completed Aug. 16, 2007 for International Application No. PCT/US2007/005098, filed Feb. 27, 2007, 5 pgs.
International Search Report, dated Mar. 20, 2009, for PCT International Application No. PCT/US08/82473, filed Nov. 5, 2008.
Japanese Patent Application No. 2011-534926: Office Action dated Oct. 30, 2013, 7 pages.
Japanese Patent Application No. 2011-534928: Office Action dated Sep. 30, 2013, 11 pages.
Joint Claim Construction Brief, In the United States District Court for the District of Delaware, Civil Action No. 1:11-;,v-00652-LPS, Jun. 14, 2012, 97 pages.
Jonbergen et al., "Anterior CervicalInterbody fusion with a titanium box cage: Early radiological assessment of fusion and subsidence", The Spine Journal 5, Jul. 2005, 645-649.
Jost, Compressive Strength of Interbody Cages in the Lumbar Spine: the Effect of Cage Shape, Posterior Instrumentation and Bone Density, 7 Eur. Spine J. 132-141, 1998.
Jury Trial Demanded, In the United States District Court for the District of Delaware, Case No. 1:11-cv-00652-LPS, filed Jul. 22, 2011,8 pages.
Jury Verdict Form, United States District Court District of Delaware, Civil Action No. 1:11-cv-00652-LPS, Jun. 14, 2013, 20 pages.
Kastner, Advanced X-Ray Tomographic Methods for Quantitative Charecterisation of Barbon Fibre Reinforced Polymers, 4th Annual Intern. Symposium on NDT in Aerospace, 2012, 9 pages.
Khan, Chapter 2—Implantable Medical Devices, Focal Controlled Drug Delivery, Advances in Delivery Science and Technology, A.J. Domb and W. Khan (eds.) 2014.

\* cited by examiner

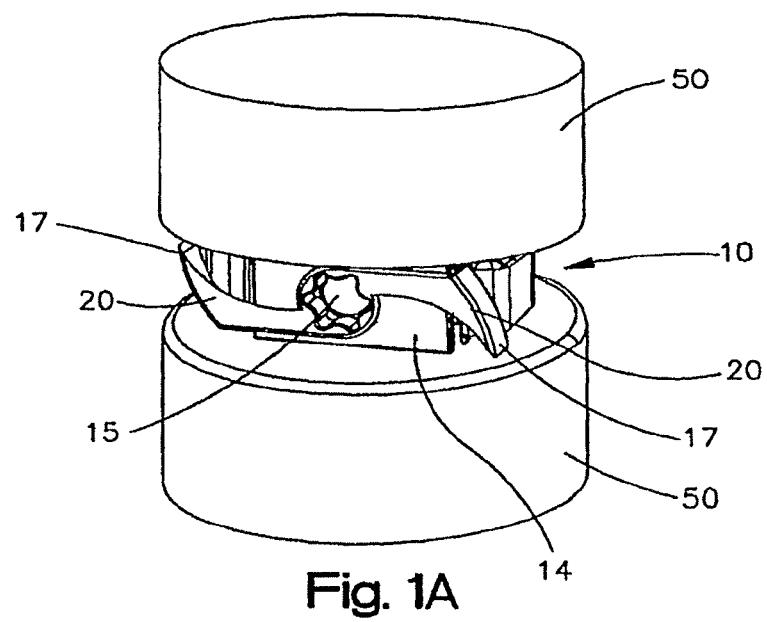
Fig. 1A
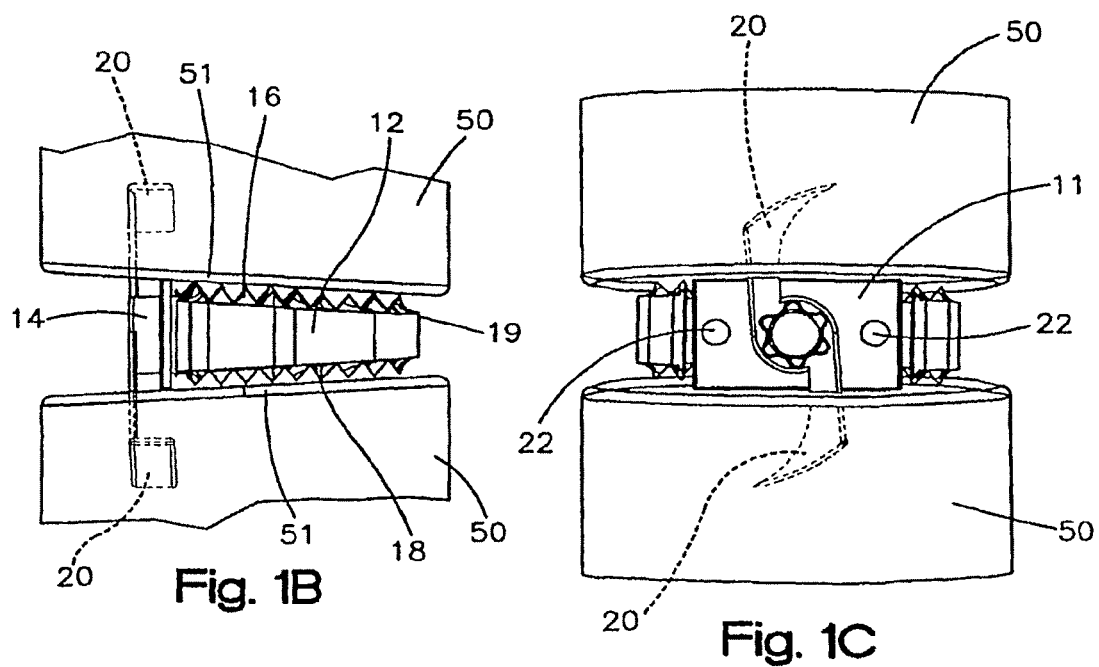
Fig. 1B
Fig. 1C

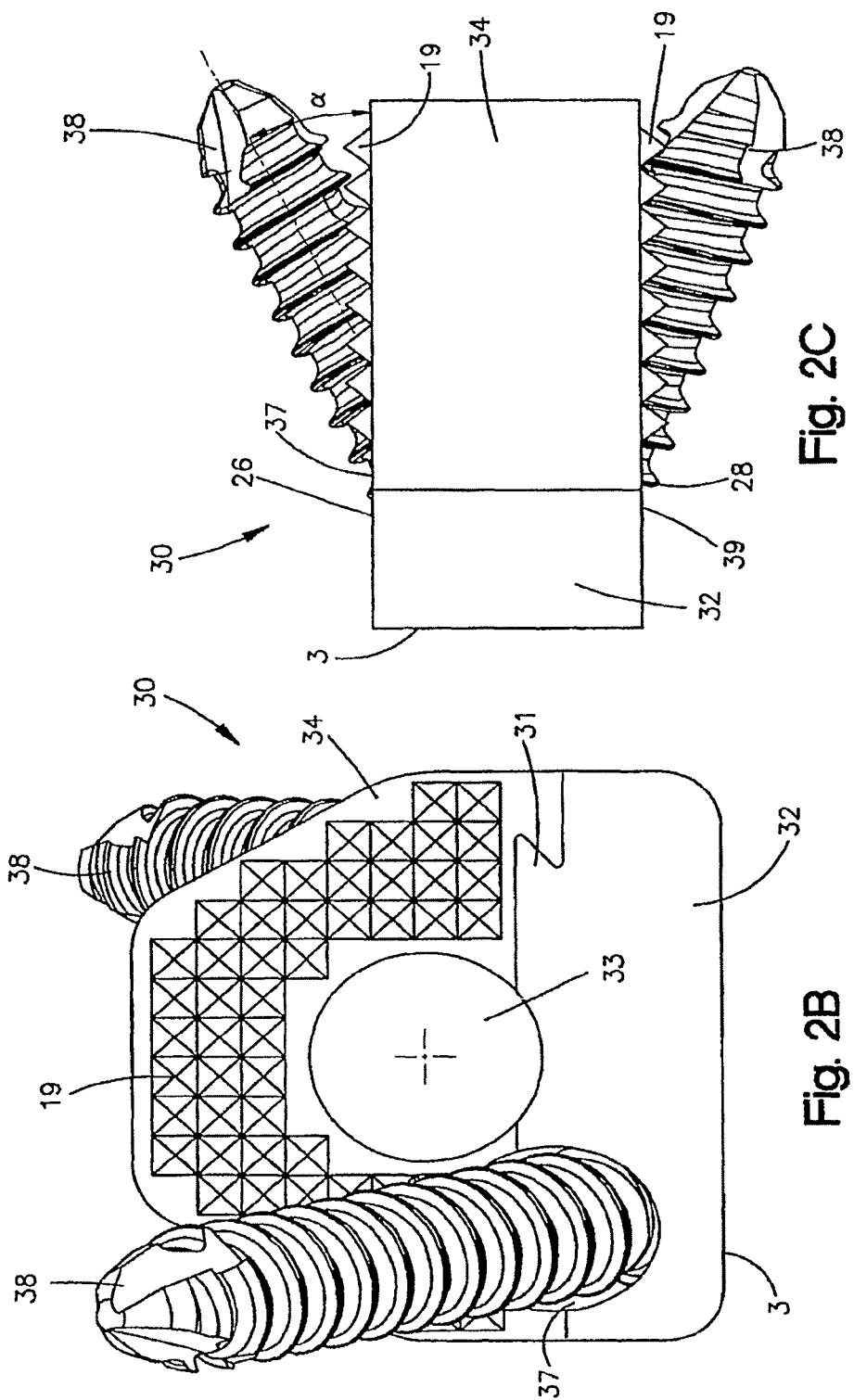

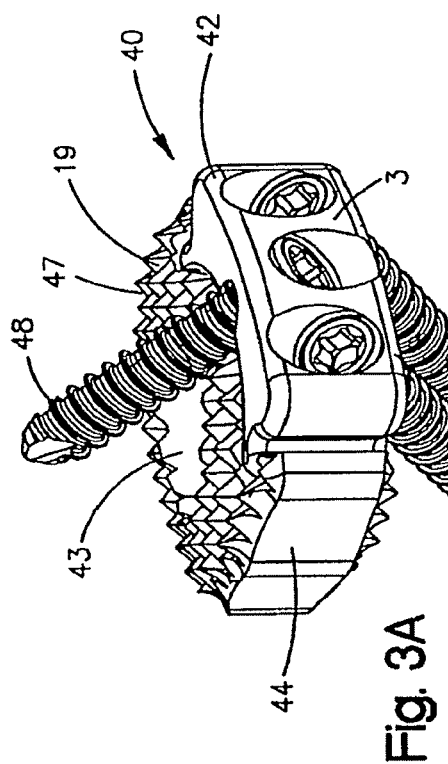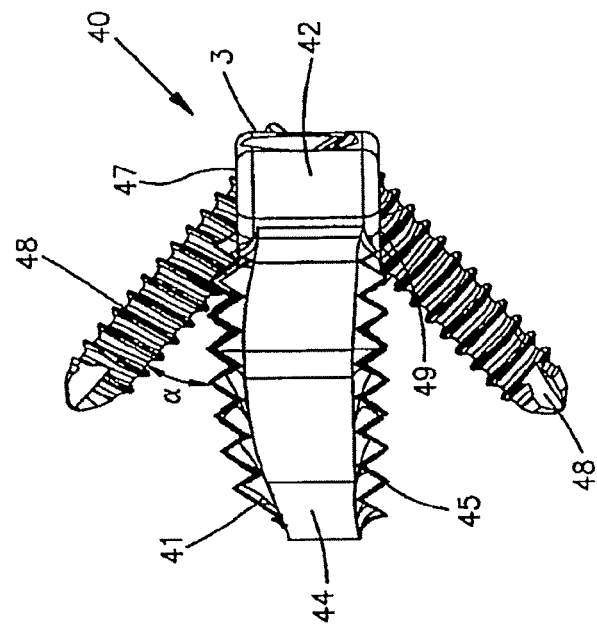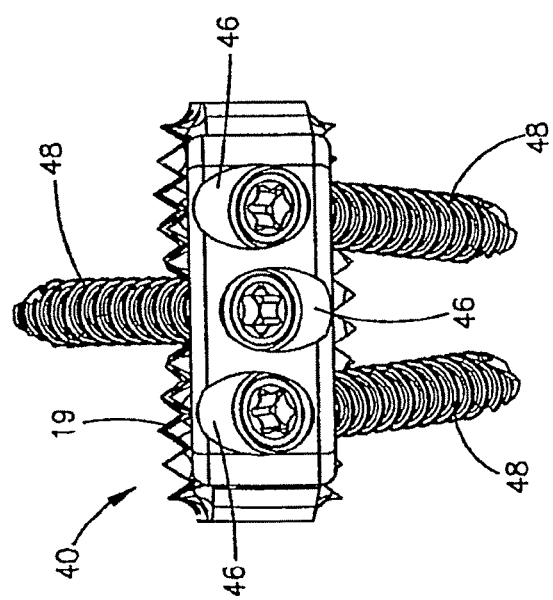

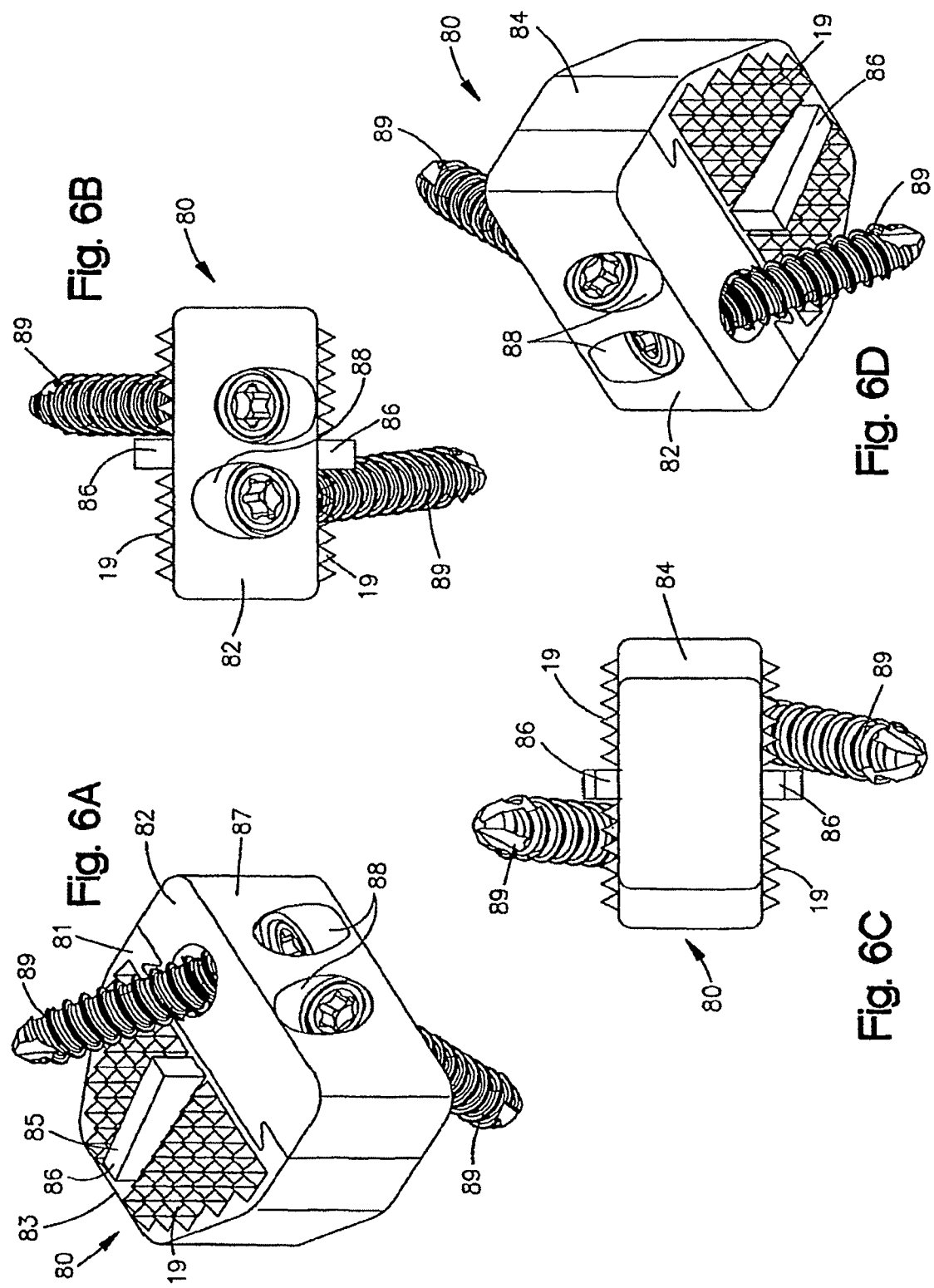

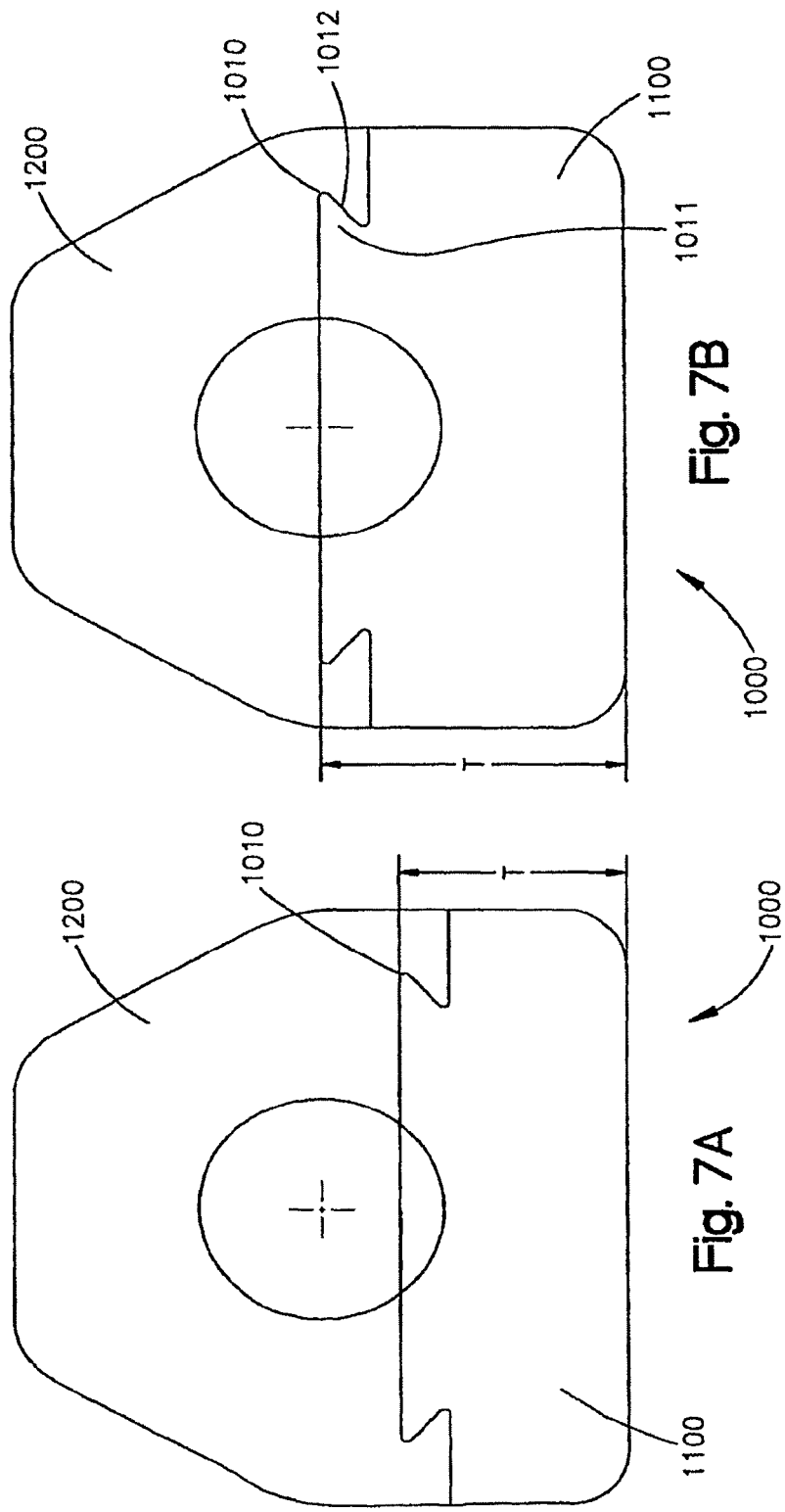

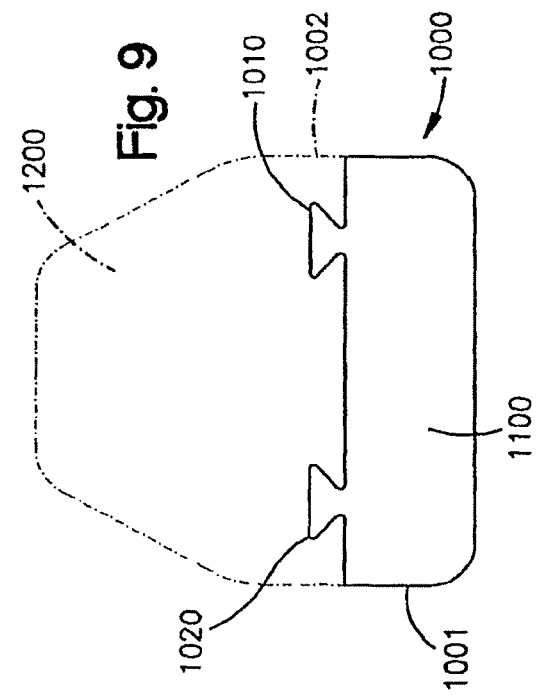
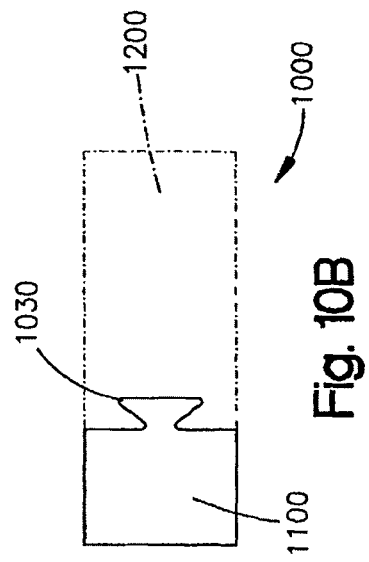
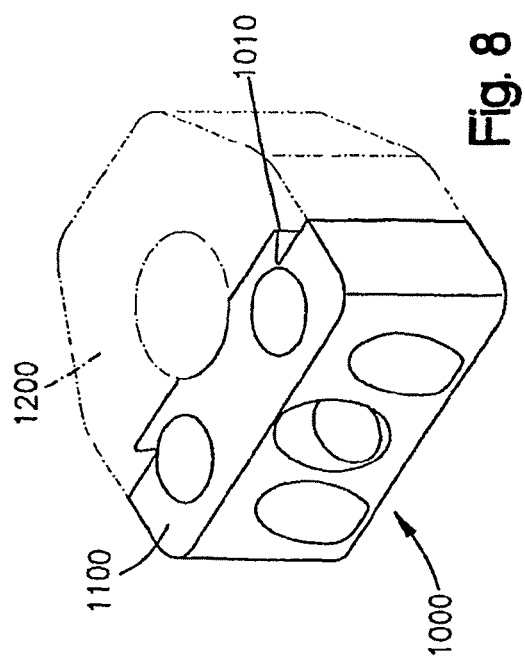
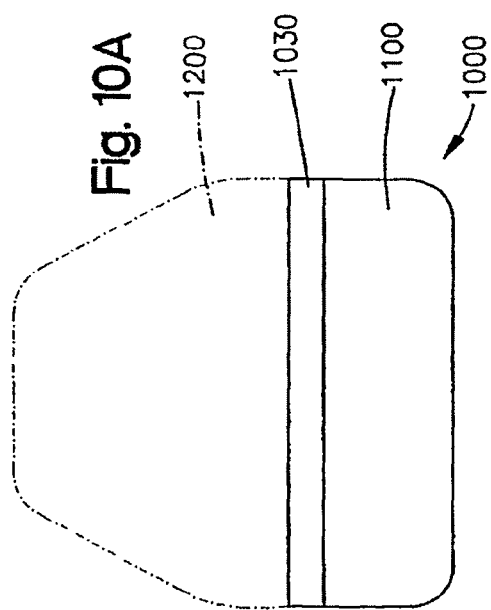

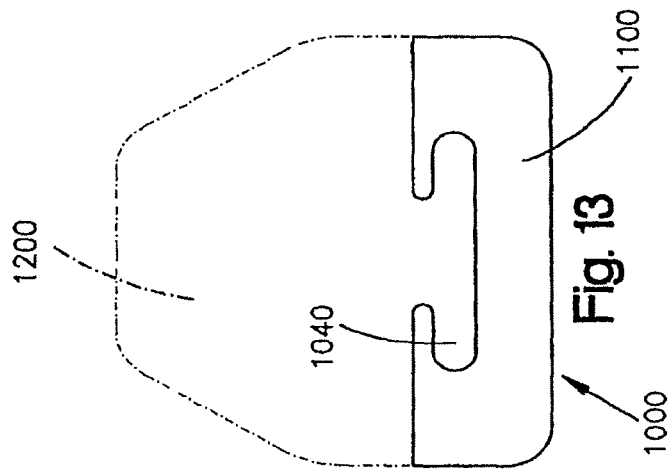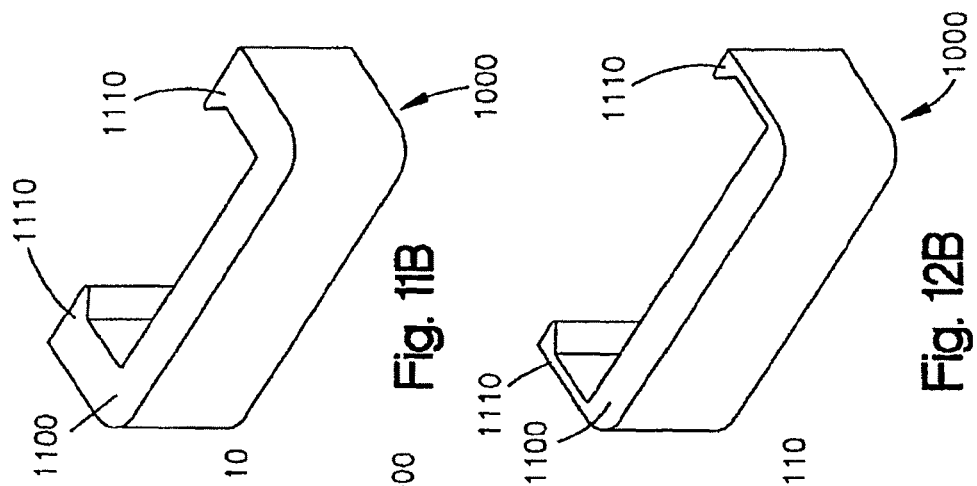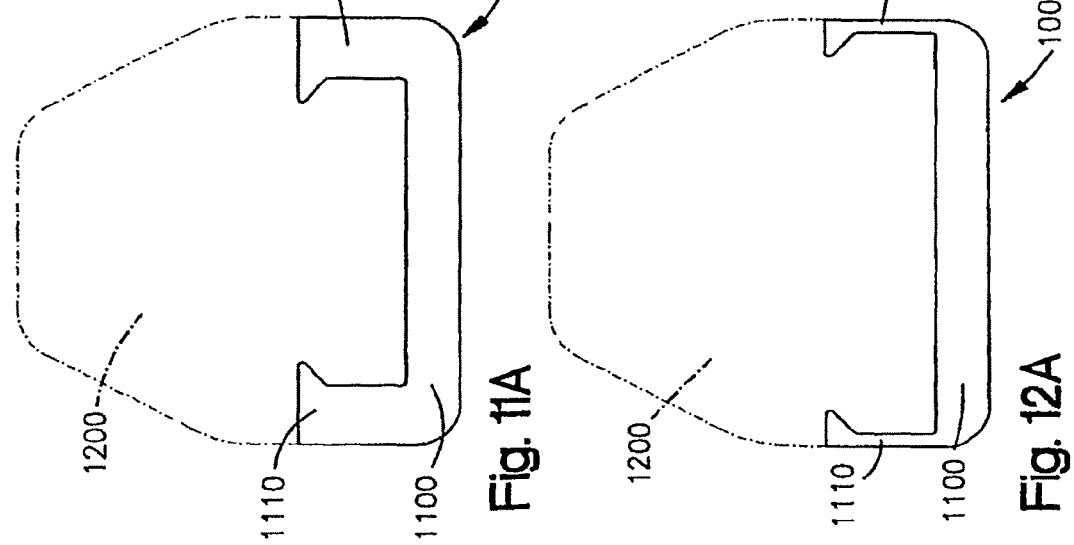

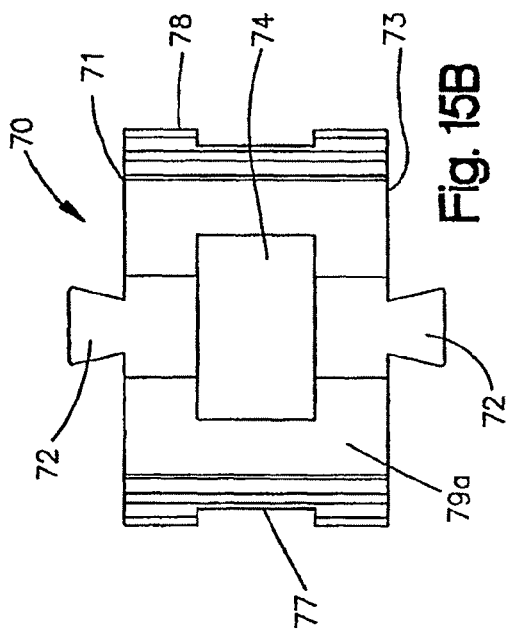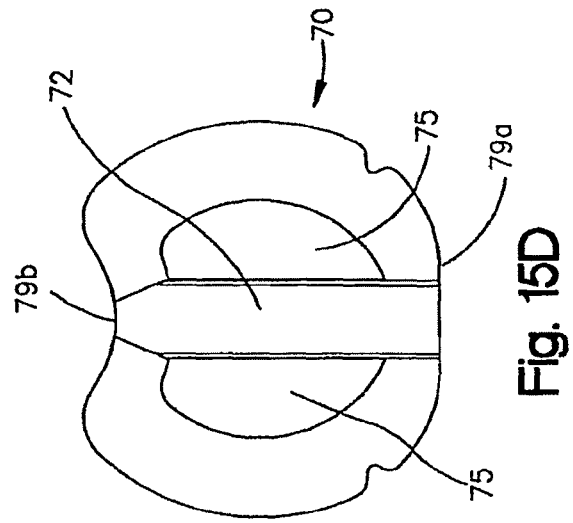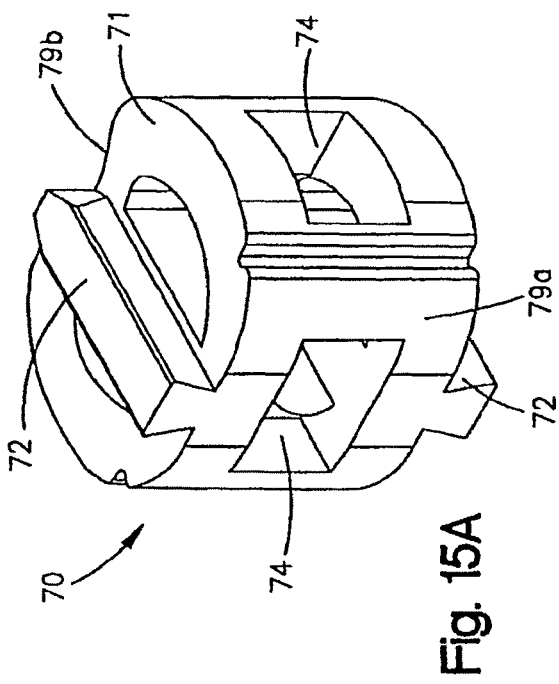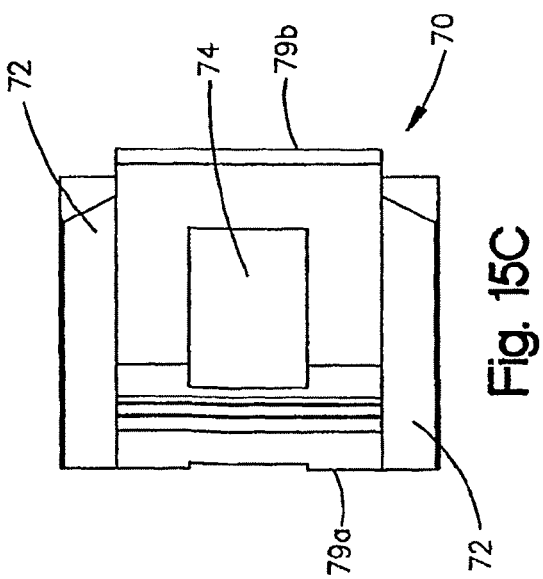

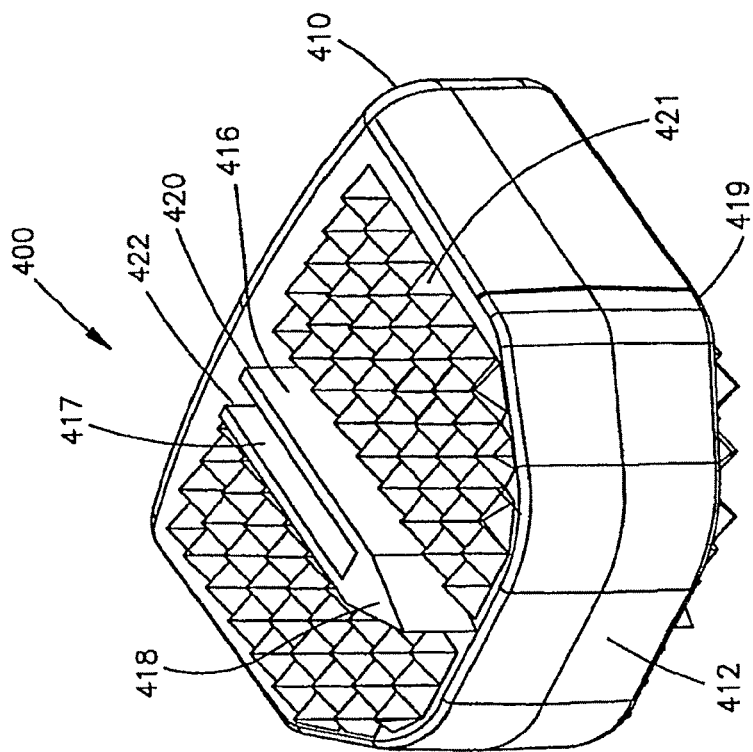
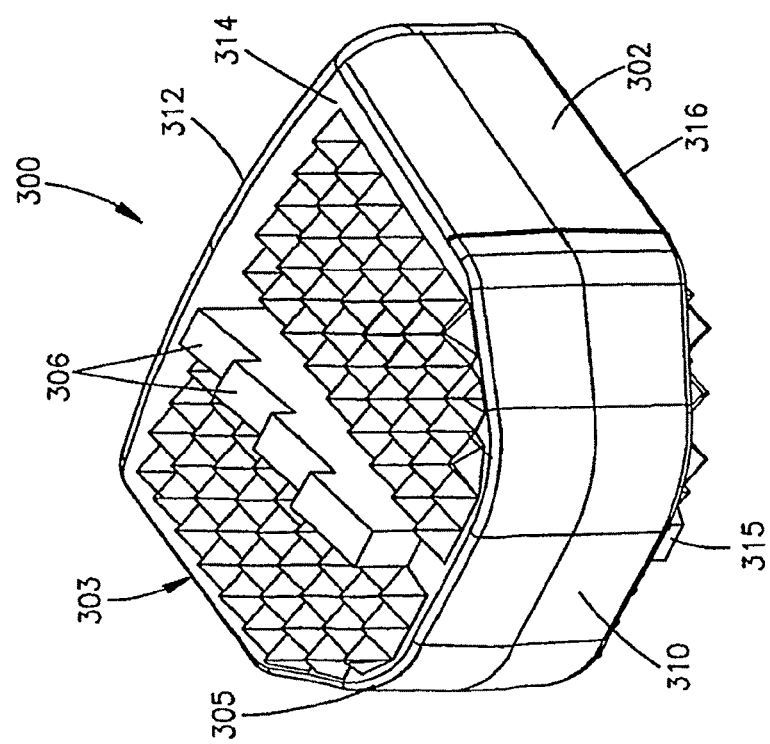

INTERVERTEBRAL IMPLANT WITH FIXATION GEOMETRY

CROSS-REFERENCE TO RELATED APPLICATIONS

This application is a continuation of U.S. patent application Ser. No. 14/997,014 filed Jan. 15, 2016, which is a divisional of U.S. patent application Ser. No. 14/166,979 filed Jan. 29, 2014, which is a continuation of U.S. patent application Ser. No. 12/280,917 filed Jul. 8, 2010, which claims the benefit of International Application No. PCT/US2007/005098 filed Feb. 27, 2007, which claims priority to U.S. Provisional Application Nos. 60/777,732 filed Feb. 27, 2006, 60/777,663 filed Feb. 27, 2006, and 60/838,229 filed Aug. 16, 2006, the entire contents of which are expressly incorporated herein by reference.

FIELD OF THE INVENTION

The present invention relates generally to intervertebral implants, and, more particularly, to a zero or low profile fusion implant including a retention mechanism that preferably provides integrated fixation geometry.

BACKGROUND OF THE INVENTION

Implants for use in spinal fusion surgery are known in the art. Such implants are used to stabilize and immobilize the spinal segments in the treatment of degenerative disc disease (single and multi-level), spinal stenosis, and failed previous fusions. Some implants use supplemental fixation means, such as a plate and screws, to retain the implant once introduced between two vertebrae.

SUMMARY OF THE INVENTION

The present invention preferably provides for an integrated retention mechanism and spacer implant construction. As such, the implant of the present invention preferably may be inserted using a one-step implantation process, as compared to a two-step process. The present invention preferably allows for implantation of an intervertebral implant and fusion of adjacent vertebrae without the need for additional supplemental fixation means. Preferably, such an implant will minimize dysphasia and irritation of soft tissue, provide sufficient segmental stability in flexion, extension and rotation, provide adequate graft retention, allow for reduced surgery times, minimize surgical trauma, and still allow for additional anterior and/or posterior fixation, if necessary. In one embodiment, the implant may comprise a spacer having a first insertion end portion, a second end portion opposite the first insertion end portion, a first lateral side portion, a second lateral side portion, an upper surface, and a lower surface. The spacer configured and dimensioned for insertion between vertebrae. The Spacer may optionally have one or more keels formed on one of the upper and lower surfaces of the spacer. The keel preferably extends from the first insertion end portion toward the second end portion at least about 50 percent of the distance between the first insertion end portion and the second end portion. Preferably, the keel extends at least about 80 percent, and more preferably 95 percent of the distance between the first insertion end portion and the second end portion.

The keel may have a first insertion end and a second end where the first insertion end may be wedge shaped. The keel may have a plurality of projections that are saw-tooth shaped. The keel may have a first insertion end and a second end portion and the first insertion end of the keel starts at about the first insertion end portion of the implant. The keel may be tapered so that it is higher at its second end relative to the insertion end. The keel preferably has a height of about 1 mm to about 3.5 mm and preferably a width of about 0.5 mm to about 3 mm.

The implant in one embodiment may be formed of an anterior plate secured to the second end portion of the spacer, the plate formed of a different material than the spacer. The plate is preferably formed of a metallic material and the spacer is preferably formed of a non-metallic material. The plate may include at least two through holes, the at least two holes configured to receive screws for securing the implant to adjacent vertebrae and defining first and second hole axes; wherein the first through hole exits through the upper surface and the second through hole exits through the lower surface, and the axes of the first and second through holes form non-zero angles with respect to the upper and lower surfaces.

The plate preferably does not extend beyond the perimeter of the spacer, and more preferably the height of the plate is no more than the height of the spacer at the second end so that the plate does not increase the height profile of the spacer. In this manner the Spacer-plate construct may have a low profile. The through holes in the plate at its outer surface may be generally aligned along a straight line that generally corresponds with the mid-plane of the implant. The spacer and plate preferably are secured together before insertion into the spine. In one embodiment the plate and spacer are connected by at least one dovetail connection, the dovetail connection preferably extends from the upper surface to the lower surface, although the dovetail may extend in a horizontal direction when the spacer is inserted in the spine. The spacer may be solid, or alternatively the spacer may have vertical or horizontal windows or channels. The spacer or plate and spacer construct may have a plurality of projections formed on at least the upper or lower surface, the projections preferably having a height less than the height of the keel. The keel in one embodiment may be formed only on the spacer.

In yet another embodiment the intervertebral implant may comprise a spacer having a first insertion end portion, a second end portion, a first lateral side portion, a second lateral side portion, an upper surface, and a lower surface, wherein the spacer configured and dimensioned for insertion between vertebrae; a plate secured to the first end of the spacer, the plate including at least two through holes defining first and second central hole axes, the at least two holes configured and dimensioned to receive screws for securing the implant to adjacent vertebrae; and at least one keel extending along the upper or lower surface and extending at least 50% of the length of the upper or lower surface between the insertion end portion and the second end portion, wherein the first and second central hole axes form non-zero angles with respect to the upper and lower surfaces of the spacer.

In another embodiment, the intervertebral implant may comprise a spacer having a first insertion end portion, a second end portion, an upper surface, and a lower surface, wherein the spacer is configured and dimensioned for insertion between vertebrae; a Plate secured to the second end portion of the spacer, the plate including one or more blades, preferably two blades, configured and dimensioned to penetrate adjacent vertebrae; and an actuator for causing the one or more blades to move to penetrate adjacent vertebrae. The one or more blades may be configured to rotate from a first position wherein the blades preferably are adjacent the plate to a second position wherein the blades preferably are not adjacent the plate. The blades preferably are configured to provide compression between the vertebrae and the implant as the blades are rotated into the second position. The implant may further comprise a locking mechanism to prevent the blades from rotating back to the first position.

BRIEF DESCRIPTION OF THE DRAWINGS

The intervertebral implant is explained in even greater detail in the following exemplary drawings. The drawings are merely exemplary to illustrate the structure of preferred implants and certain features that may be used singularly or in combination with other features. The invention should not be limited to the embodiments shown.

FIG. 1A is a perspective view of an intervertebral implant according to one embodiment of the present invention positioned between adjacent vertebral bodies;

FIG. 1B is a side view of the implant shown in FIG. 1A;

FIG. 1C is a front view of the implant shown in FIG. 1A;

FIG. 2B is a top view of the implant shown in FIG. 2A;

FIG. 2C is a side view of the implant shown in FIG. 2A;

FIG. 3A is a perspective view of an intervertebral implant employing three retention screws according to still another embodiment of the present invention;

FIGS. 3B and 3C are front and side views, respectively, of the implant shown in FIG. 3A;

FIG. 6A is a perspective view of an intervertebral implant employing top and bottom keels and two retention screws according to still another embodiment of the present invention;

FIGS. 6B and 6C are front and back views, respectively, of the implant shown in FIG. 6A;

FIG. 6D is another perspective view of the implant shown in FIG. 6A;

FIGS. 7A and 7B are top views of an implant employing a dovetail connection between a plate and spacer;

FIG. 8 is a perspective view of an implant employing a dovetail connection between a plate and spacer;

FIG. 9 is a top view of an implant employing two dovetail connections between the plate and spacer;

FIGS. 10A and 10B are top and side views, respectively, of an implant employing a dovetail connection running horizontally between the plate and spacer;

FIGS. 11A and 12A are top views of implants employing a plate and spacer where the plate sides wrap around a portion of the spacer;

FIGS. 11B and 12B are perspective views of the plates of FIGS. 11A and 12A, respectively;

FIG. 13 is a top view of an implant employing a "jigsaw puzzle" connection between the plate and spacer;

FIG. 15A is a perspective view of an intervertebral implant employing top and bottom keels according to yet another embodiment of the present invention;

FIGS. 15B-15D are front, side and top views, respectively, of the implant depicted in FIG. 15A;

FIG. 18 is a perspective view of an intervertebral implant employing top and bottom keels according to yet another embodiment of the present invention; and FIG. 19 is a perspective view of an intervertebral implant employing top and bottom keels according to still another embodiment of the present invention.

DETAILED DESCRIPTION OF THE PREFERRED EMBODIMENTS

Figure 2A:
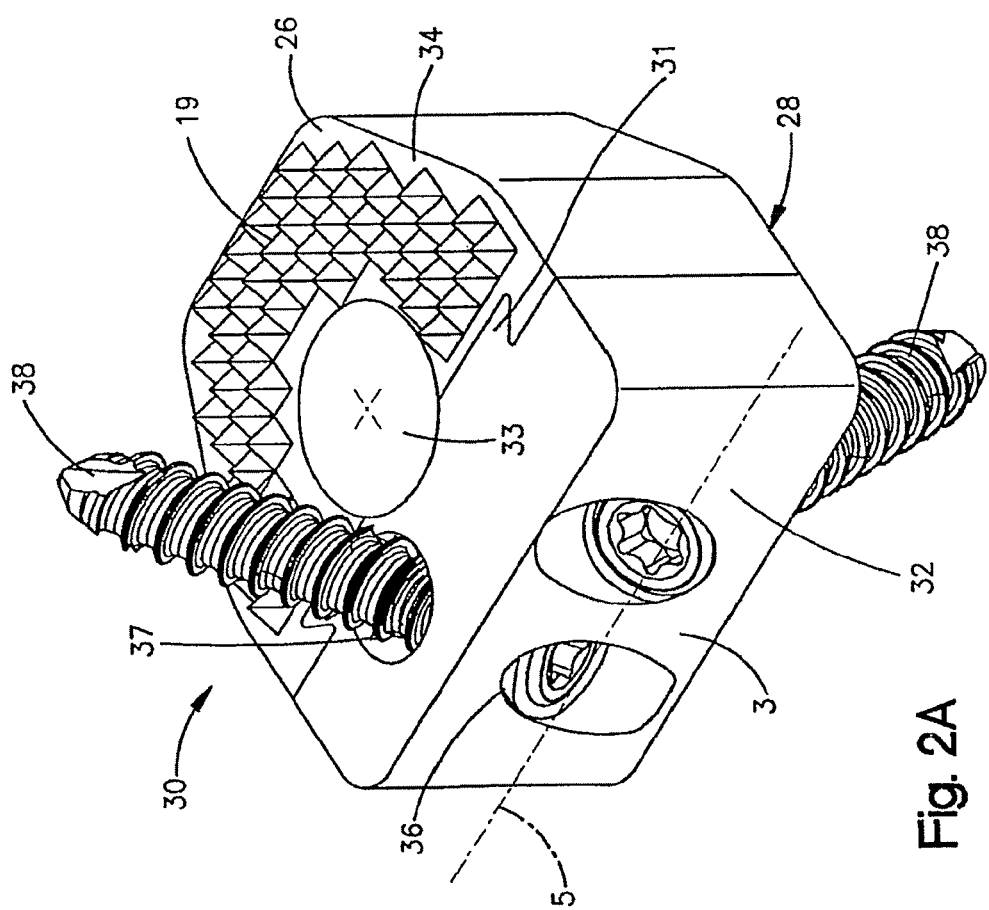
FIG. 2A is a perspective view of an intervertebral implant employing two retention screws according to another embodiment of the present invention.

Referring generally to FIGS. 1A, 1B and 1C, an intervertebral implant 10 according to an embodiment of the present invention is illustrated. As known in the art, the implant 10 is inserted between adjacent vertebra (shown schematically as 50 in FIGS. 1A-1C) of the spinal column. In this embodiment, the implant includes a plate 11 and a graft/spacer 12 combined with a retention mechanism 14. As shown, implant 10 includes an upper surface 16 and a lower surface 18, which may taper, be curved, arcuate or flat as desired or to conform to the end plates of the vertebrae and the intervertebral space. As shown, upper and lower surfaces 16, 18 may include a series of teeth or similar projections 19 to aid in securing the implant to the vertebral endplates.

In addition, the implant includes retention mechanism 14 which preferably has two wedge-shaped blades 20, although more or less blades 20 may be included. Following implantation between vertebrae, retention mechanism 14 is torsionally driven into vertebral bodies 50 and rotationally locked. More particularly, wedge-shaped blades 20 may be rotated to engage, penetrate or cut through the endplates of vertebral bodies 50 to hold implant 10 in position. Wedges 20 preferably are pointed and shaped to facilitate penetrating the end plates. Preferably, retention mechanism has a recess 15 or projection (not shown) to receive a tool to rotate retention mechanism 14 relative to plate 11 and spacer 12. Preferably, retention mechanism 14 includes a locking mechanism to prevent rotation of blades 20 or otherwise lock the position of the blades 20 in the vertebrae. Retention mechanism 14 may have a hub (not shown) that projects into and is held in a cavity (not shown) in the plate 11. The hub is held or retained in the cavity, but may rotate relative to the plate. Recess 15 is preferably star-shaped and formed in the hub.

In the insertion position the pointed tips 17 on the blades 20 are directed toward the vertebrae. In the embodiment shown, one pointed tip 17 is directed toward the superior vertebrae and one pointed tip 17 is directed toward the inferior vertebrae. After the implant 10 is positioned between the vertebrae, the retention mechanism is rotated clockwise so that the pointed tips 17 preferably are directed in the lateral/medial direction. In the preferred embodiment, the retention mechanism is rotated approximately 90°, although the retention mechanism may be rotated by more or less angular amounts. As the blades are rotated they engage, penetrate into, or cut through the vertebrae. The blades are preferably wedge-shaped and preferably compress the adjacent vertebrae together or towards one another as they are rotated.

Implant 10 may also include openings 22 for additional fixation screws, if necessary. Openings 22 may also permit screws that permit the plate 11 to be attached to the spacer 12. Both plate 11 and graft/spacer 12 may be formed of PEEK, titanium, titanium alloy, stainless steel, allograft bone or any other suitable, biocompatible material. Preferably plate 11 and retention mechanism 14 are formed of metal or metal alloy and the spacer is formed of PEEK or other polymer, or alternatively bone or ceramic or radiolucent biocompatible material. Screws not shown) may be formed of titanium, titanium alloy or stainless steel. Graft/spacer 12 may include one or more openings (not shown) designed to receive bone graft material.

Reference is now made to FIGS. 2A, 2B and 2C, which show an intervertebral implant 30 according to another embodiment of the present invention. Implant 30 includes a plate 32 and a spacer/graft 34. As shown, in this embodiment, the retention mechanism is provided by screws that provide opposing screw fixation. In other words, for example, one screw diverges outward such that it is secured into an upper or superior vertebra and another screw diverges outward from the implant such that it is secured in a lower or inferior vertebra so that opposing forces act on the plate and/or vertebrae. A pair of holes or openings 36 accept two screws 38, which penetrate the vertebral bodies and secure the implant in place. One of holes 36 is angled upward toward the upper or superior vertebrae, and the other hole 36 is angled downward toward the lower or inferior vertebrae, such that holes 36 form an angle with respect to the upper and lower surfaces 26, 28 of the implant 30. As shown best in FIG. 2C, holes 36 form an angle $\alpha$ with respect to the upper and lower surfaces of the implant, where $\alpha$ may range between 20° and 50°, and preferably ranges between 30° and 45°. Angle $\alpha$ may be the same for all holes 36 or may be different for each hole. After the implant is placed between adjacent vertebrae, screws 38 are inserted through the holes 36 in plate 32 to penetrate the vertebrae and hold the implant in position, i.e., one screw is inserted into the upper vertebrae and the other is inserted into the lower vertebrae. As with the previous embodiment, upper and/or lower surfaces 26, 28 of the implant may include a series of teeth 19, or other similar projections, to aid in securing the implant to the vertebral endplates. Both plate 32 and graft/spacer 34 may be formed of PEEK, titanium, titanium alloy, stainless steel, allograft bone or any other suitable, biocompatible material, or any combination thereof. Screws 38 may be formed of titanium, titanium alloy or stainless steel. Graft/spacer 34 may include one or more openings 33 designed to receive bone graft material.

Plate 32 is preferably formed of metal or metal alloy and the spacer 34 is preferably formed of PEEK or other polymer, or bone (allograft) or ceramic or other radiolucent, biocompatible material. The plate 32 preferably is of the same height or less than the height of the spacer 12 so the implant has a low profile. The plate is preferably connected to the spacer 12 before the implant 10 is implanted. Preferably the holes 36 are formed substantially along a single substantially horizontal line 5 or plane in the plates. The line or plane along which the holes 36 are formed in the outer surface of the plate 32 is preferably substantially the midplane 5 of the implant. In the embodiment of FIGS. 2A-2C, the exit openings 37, 39 for the screw holes 36 are formed in the plate. The plate 32 is preferably connected to the spacer 34 by a dovetail joint 31 that requires the plate 32 to the slide vertically relative to the spacer 34.

Figure 4A:
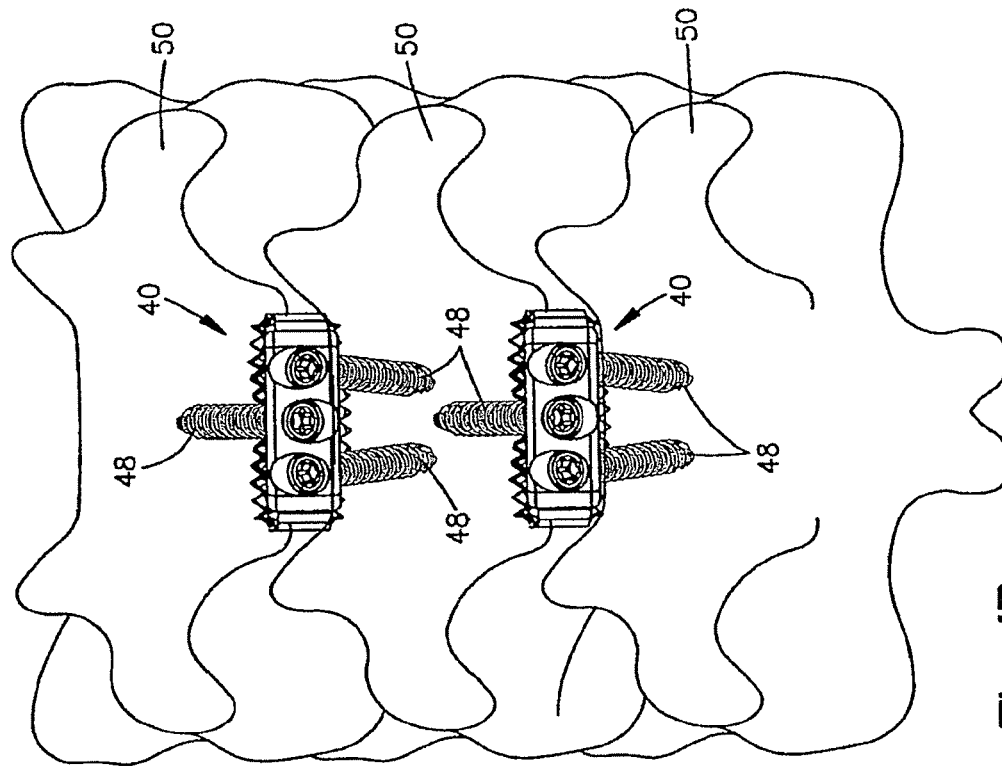
FIGS. 4A and 4B are side and front views, respectively, of the implant shown in FIG. 3A, in position between vertebrae.
Figure 4B:
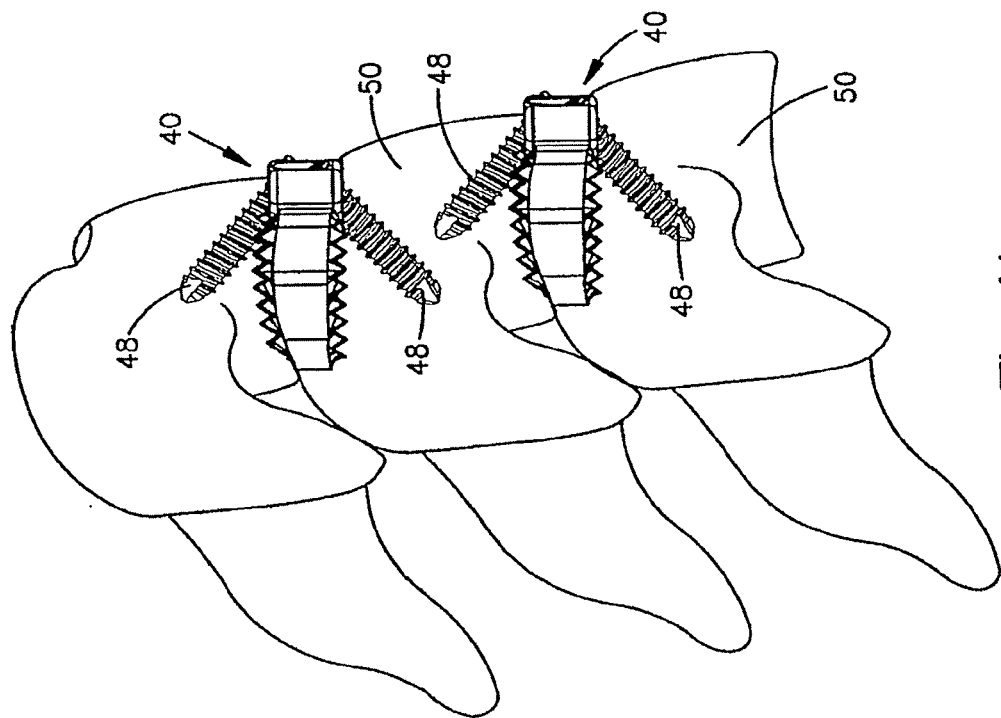

Reference is now made to FIGS. 3A, 3B and 3C, which show an intervertebral implant 40 according to still another embodiment of the present invention. As with the embodiment shown in FIG. 2A, implant 40 includes a plate 42 and a spacer/graft 44, and the retention mechanism is provided by screws that provide opposing screw fixation. As shown, three holes 46 accept three fixation screws 48, which penetrate the vertebral bodies and secure the implant in place, as shown in FIGS. 4A and 4B. As shown best in FIG. 3C, holes 46 form an angle $\alpha$ with respect to the upper and lower surfaces 41, 45 of the implant, where $\alpha$ may range between 20° and 50°, and preferably ranges between 30° and 45°. Angle $\alpha$ may be the same for all holes 46 or may be different for each hole. After the implant is placed between adjacent vertebrae, screws 48 are inserted through the holes 46 in plate 42 to penetrate the vertebrae and hold the implant in position. In this embodiment, one screw 48 penetrates the upper vertebrae and two screws 48 penetrate the lower vertebrae. As with the previous embodiment, upper and/or lower surfaces 41, 45 of the implant 40 may include a series of teeth 19, or other similar projections, to aid in securing the implant to the vertebral endplates. Both plate 42 and graft/spacer 44 may be formed of PEEK, titanium, titanium alloy, stainless steel, allograft bone or any other suitable, biocompatible material, or any combination thereof. Screws 48 may be formed of titanium, titanium alloy or stainless steel. Graft/spacer 44 may include one or more openings 43 designed to receive bone graft material.

Plate 42 is preferably formed of metal or metal alloy and spacer 44 is preferably formed of PEEK, other polymer, bone, ceramic or other radiolucent, biocompatible material. The plate 32 preferably is the same height or less than the height of the spacer. As with implant 30, plate 42 is preferably connected to spacer 44 prior to implantation and holes 46 are preferably formed substantially along a substantially horizontal line in the outer end surface 43 of the plate 42 at an angle $\alpha$ so that at least two fixation screws are directed in opposed directions, one toward the superior vertebrae and one toward the inferior vertebrae. In the embodiment of FIGS. 3A-3C, the exit openings 47, 49 in the superior and inferior surfaces for the screws are preferably formed at the junction of the plate and spacer, or in the spacer. Alternatively, like the embodiment of FIGS. 2A-2C, the exit openings 47, 49 may be formed entirely with in the plate 42.

The superior surface, the inferior surface or both surfaces of the spacer and the implant construct may have a curved surface to help provide the proper shape to the spine. The particular surface shape and curvature, or taper in the anterior-posterior direction as well as between the lateral side surfaces will depend upon the location the spacer is intended to be inserted. The shape of the perimeter of the spacer shown in FIGS. 2-14 are generally for cervical applications and the spacer may have an alternative shape, such as that illustrated by the perimetral shape of FIG. 15 for other locations such as in the lumbar area of the spine.

Figure 5A:
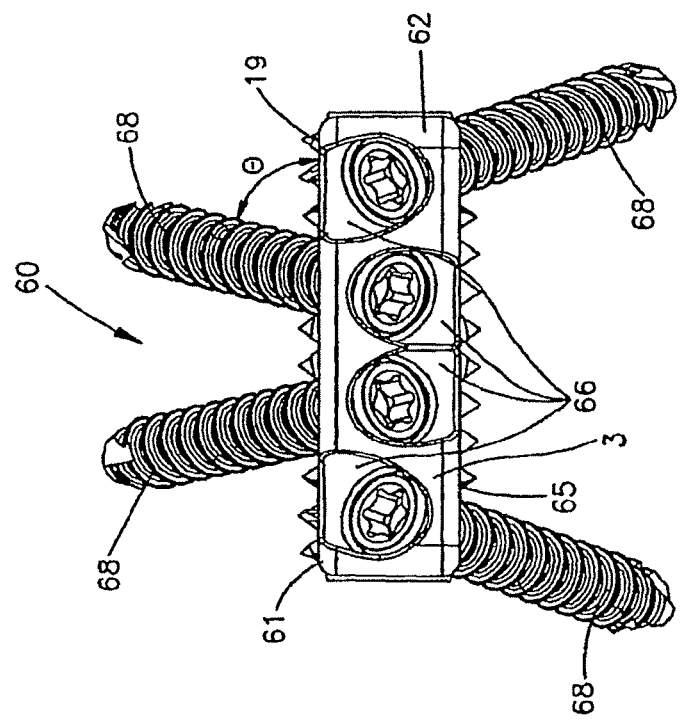
FIG. 5A is a perspective view of an intervertebral implant employing four retention screws according to still another embodiment of the present invention.
Figure 5B:
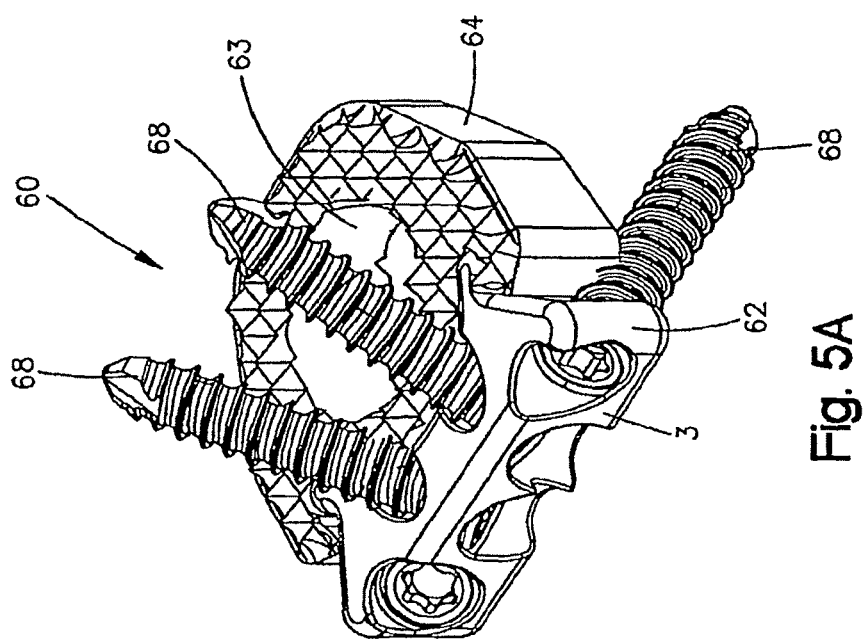
FIGS. 5B and 5C are front and side views, respectively, of the implant shown in FIG. 5A.
Figure 5D:
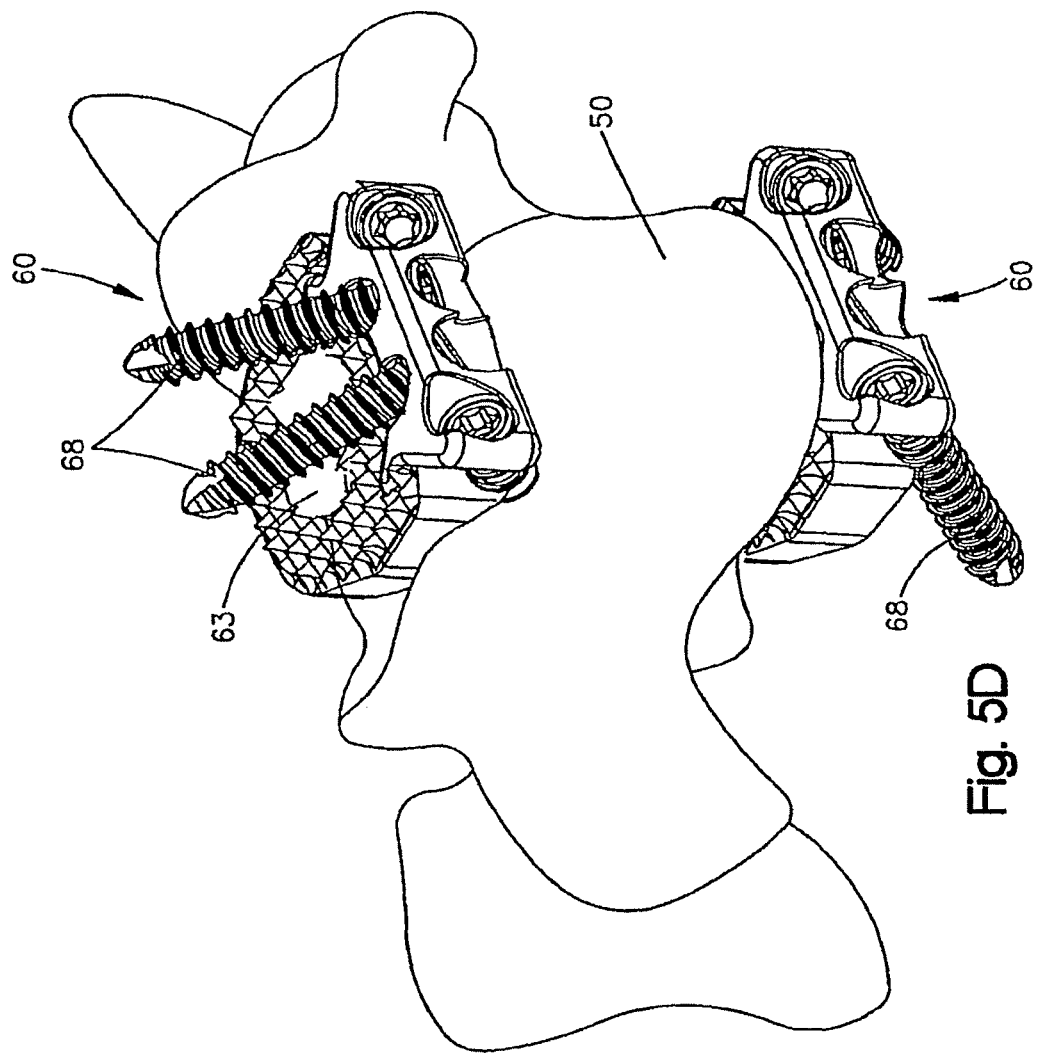
FIG. 5D is a perspective view of two of the implants of FIG. 5A positioned between vertebrae.
Figure 5C:
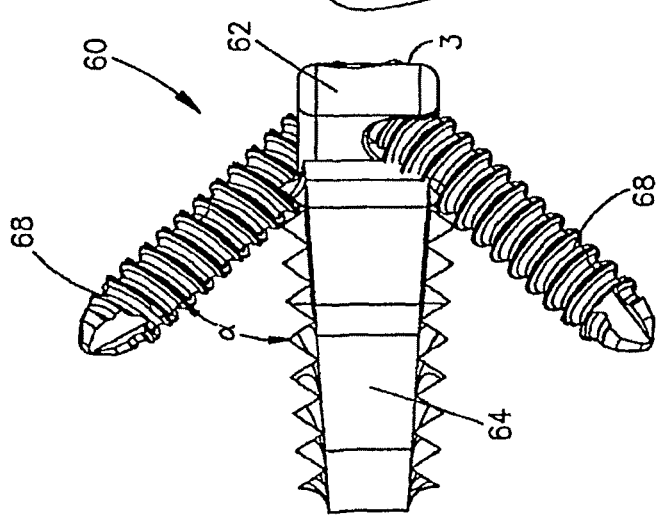

Reference is now made to FIGS. 5A, 5B and 5C, which show an intervertebral implant 60 according to still another embodiment of the present invention. As with the embodiment shown in FIG. 3A, implant 60 includes a plate 62 and a spacer/graft 64, and the retention mechanism is provided by screws which provide opposing screw fixation. As shown, four holes 66 accept four fixation screws 68, which penetrate the vertebral bodies and secure the implant 60 in place, as shown in FIG. 5D. As shown best in FIG. 5C, holes 66 form an angle α with respect to the upper and lower surfaces 61, 65 of the implant 60, where α may range between 20° and 50°, and preferably ranges between 30° and 45°. Angle α may be the same for all holes 66 or may be different for each hole. After the implant is placed between adjacent vertebrae, screws 68 are inserted through the holes 66 in plate 62 to penetrate the vertebrae and hold the implant in position. In this embodiment, the two inner screws 68 penetrate the upper vertebrae and the two outer screws 68 penetrate the lower vertebrae. As with the previous embodiment, upper and/or lower surfaces of the implant may include a series of teeth 19, or other similar projections, to aid in securing the implant to the vertebral endplates. Both plate 62 and graft/spacer 64 may be formed of PEEK, titanium, titanium alloy, stainless steel, allograft bone, or any other suitable, biocompatible material, or any combination thereof. Screws 68 may be formed of titanium, titanium alloy or stainless steel. Graft/spacer 64 may include one or more openings 63 designed to receive bone graft material. Preferably the plate 62 is formed of a metal or metal alloy and the spacer 64 is formed of PEEK, other polymer, bone allograft, ceramic or other radiolucent biocompatible material. The holes 66 are formed in the outer surface 3 of the end wall of the plate 62 substantially along a horizontal line or plane at an angle α.

The screw holes 66 in the plate 62 preferably are directed outward from the center of the implant, preferably at an angle .theta.. The screw hole openings and configurations, as well as the screws may have the configuration and construction and materials described in US2005/0177236 which is incorporated by reference herein in its entirety. The screws inserted in the embodiments of FIGS. 5A-5C do not intersect a vertical plane cutting the implant 60 into two substantial halves. The screws, and the screw holes, in the embodiment of FIGS. 5A-5C on the left side, one of which extends in the superior direction and the other which extends in the inferior direction may extend laterally outward from the center plane at different angles .theta., or at the same angle .theta.. Preferably the two outermost holes 66 in the implant 60 extend toward the inferior vertebrae while the two inner screw holes 66 extend toward the superior vertebrae.

FIGS. 6A-D show an intervertebral implant 80 according to yet another embodiment of the present invention. As with the embodiments shown in FIGS. 2A, 3A and 5A, implant 80 includes a plate 82 and a spacer/graft 84. However, in this embodiment, the retention mechanism is provided by a combination of opposing keels 86 on the top and bottom surfaces 81, 85 and screws providing opposing screw fixation. The upper and lower keels 86 provide additional additive resistance to torsion or rotation of the implant. As shown, in addition to upper and lower keels 86, a pair of holes 88 accept two fixation screws 89, which penetrate the vertebral bodies and secure the implant in place. As with previous embodiments, holes 88 form an angle α with respect to the upper and lower surfaces of the implant, where α may range between 20° and 50°, and preferably ranges between 30° and 45°. Angle α may be the same for all holes 88 or may be different for each hole.

After the implant is placed between adjacent vertebrae, screws 89 are inserted through the holes 88 in plate 82 to penetrate the vertebrae and aid in holding the implant in position. As with previous embodiments, upper and/or lower surfaces 81, 85 of the implant 80 may include a series of teeth 19, or other similar projections, to aid in securing the implant to the vertebral endplates. Preferably, the keel 86 is at least as high as the teeth or protrusions 19. The keel preferably may have a height of about 1 mm to about 3.5 mm. The keel 86 may have the shape shown in FIG. 86, although it may have the shapes shown in FIGS. 15-19, or other shapes. The keel 86 preferably extends in the anterior-posterior direction. The leading end 85 of the keel may be pointed or tapered so that it gets wider from the posterior end 83 to the anterior end 83. The keel preferably may be about 0.5 mm to about 3.0 mm wide. The keel may also get higher as it extends from the posterior end to the anterior end. The taper in the height and width may permit easier insertion of the implant.

The keel 86 may only extend along the spacer as shown, or may extend along the spacer 84 and plate 82. The length of the keel may be, and preferably is, greater than the width of the keel. The length of the keel 86 is preferably greater than about 50 percent of the length of the implant 80 in the posterior to anterior direction and in some embodiments preferably greater than about 80 to about 95 percent of the length of the implant 80 in the anterior-posterior direction.

Both plate 82 and graft/spacer 84 may be formed of PEEK, titanium, titanium alloy, stainless steel, allograft bone, or any other suitable, biocompatible material, or any combination thereof, while screws 89 may be formed of titanium, titanium alloy or stainless steel. Graft/spacer 84 may include one or more openings (not shown) designed to receive bone graft material. As with the earlier embodiment the plate is preferably a different material than the spacer, and the plate is preferably a metallic material whereas the spacer is a non-metallic material. A preferred embodiment for the implants 10, 30, 40, 60 and 80 may include a titanium alloy for the plate and an allograft for the spacer.

FIGS. 7A-13 depict various attachment mechanisms for attaching the plate and spacer of the implant together. The attachment mechanisms between spacer and plate are not limited to the mechanisms depicted. Various figures depict two or three holes of the retention feature of the implant. It should be noted that the number of holes two, three, or four of the retention feature of the implant is not limited by the type of attachment mechanism between the spacer and plate.

FIGS. 7A and B depict a top view of dovetail connection 1010 between plate 1100 and spacer 1200 (These figures do not depict the holes of the retention feature so as to more clearly illustrate the dovetail connection 1010). The dovetail connection 1010 may extend from the upper surface to the lower surface of the implant 1000. As shown in these figures, the thickness T of the plate 1100 may vary depending on the application. Representative values for T include about 5 mm to about 7 mm. Furthermore, the size of the dovetail connection 1010 may also vary in size, both in length and in width. As shown in FIGS. 7A and B, the male dovetail connector 1011 is formed as part of the plate 1100 while the female connector 1012 is formed on the spacer 1200. It is contemplated that the female connector may be formed on the plate and the male connector may be formed on the spacer. FIG. 8 is a perspective view of an implant 1000 with a dovetail connection 1010 between the plate 1100 and spacer 1200. In this figure, the implant 1000 includes three holes 1110 similar to the embodiment depicted in FIGS. 3A-4B.

FIG. 9 depicts an implant 1000 having two dovetail connections 1010, 1020 between the spacer 1200 and plate

1100. In this embodiment, the dovetail connections 1010, 1020 may extend between the upper surface and lower surface of the implant. It is contemplated that the dovetail connections may extend from one lateral side 1001 of the implant 1000 to the other lateral side 1002. FIGS. 10A and 10B depict such a dovetail connection between the plate 1100 and spacer 1200.

FIGS. 11 and 12 depict further embodiments of the connection between the plate 1100 and spacer 1200. In these embodiments, the sides 1110 of the plate 1100 "wrap" around the proximal end (front) of the spacer 1200. The length or thickness of the sides 1110 of the plate 1100 may vary, as depicted in the two figures, depending on the application.

FIG. 13 depicts another embodiment of the connection between the plate 1100 and spacer 1200. In this embodiment, the connection between the plate and spacer is a "jigsaw puzzle" connection 1040. The shape of the "jigsaw puzzle" connection 1040 may vary depending on the application. As with the other embodiments discussed above, the male and female connectors of the connection may be formed on the spacer 1200 or plate 1100, depending on the application.

Figure 14A:
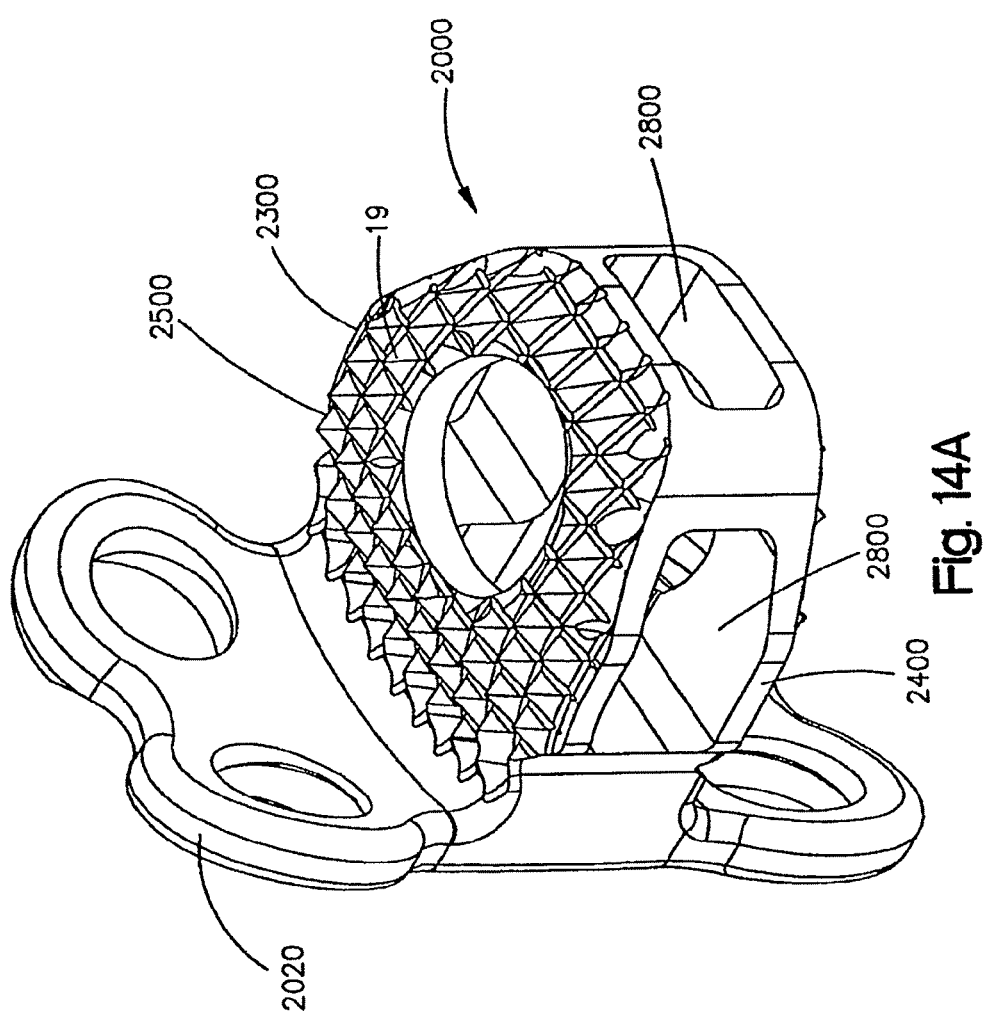
FIG. 14A is a perspective view of an implant wherein the plate and spacer are integrally formed with one another.
Figure 14C:
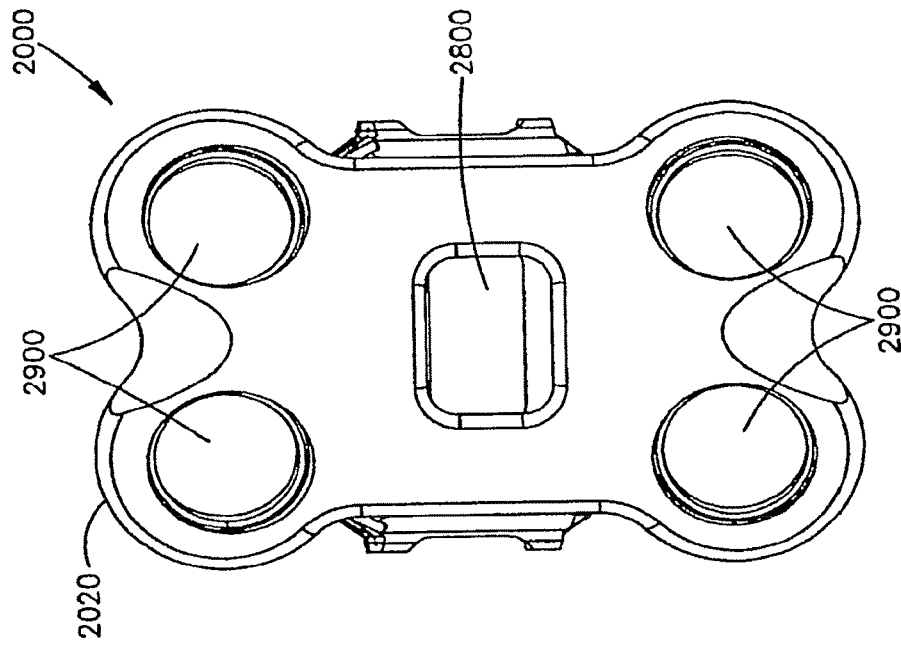
FIGS. 14B-14E are rear, front, side and top views of the implant depicted in FIG. 14A.
Figure 14B:
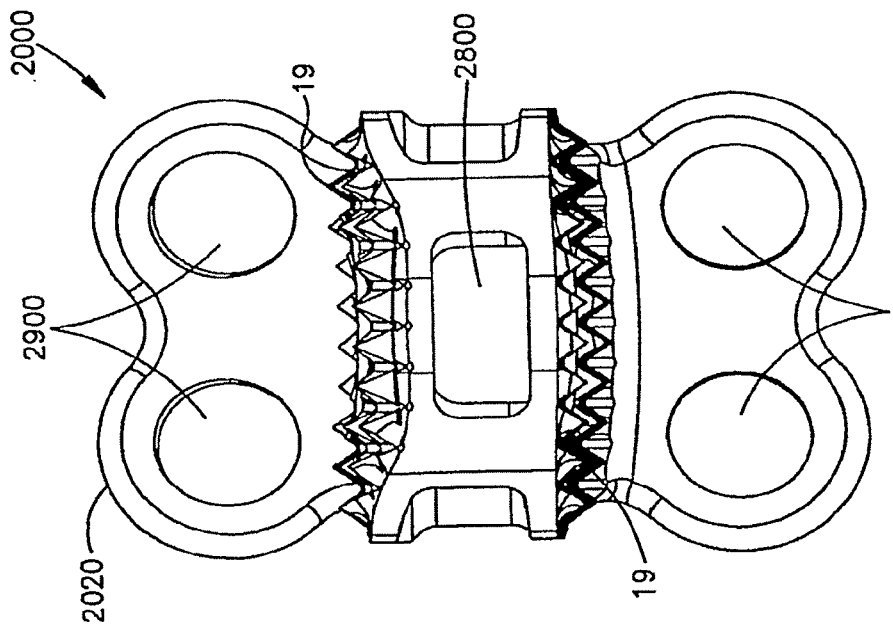
Figure 14E:
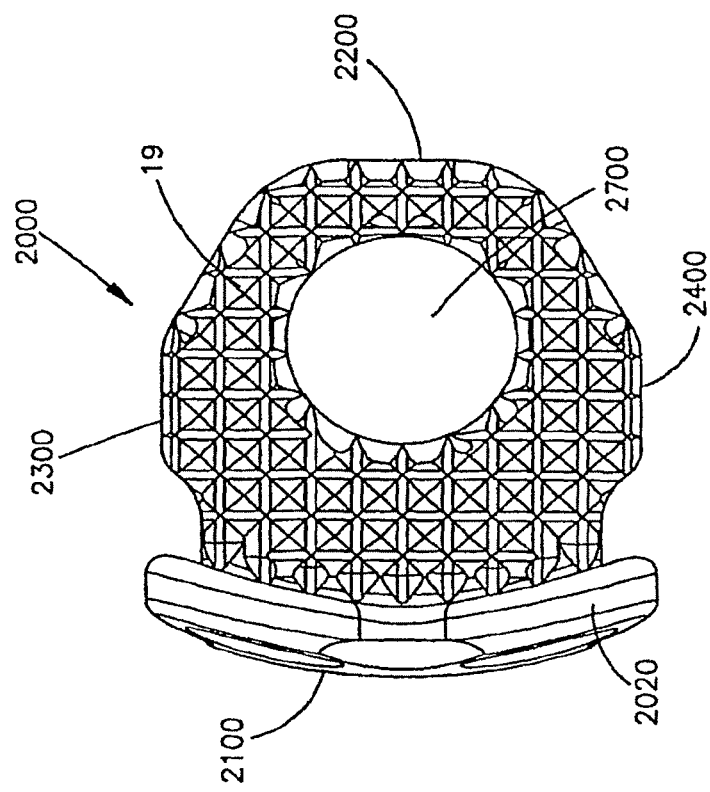
Figure 14D:
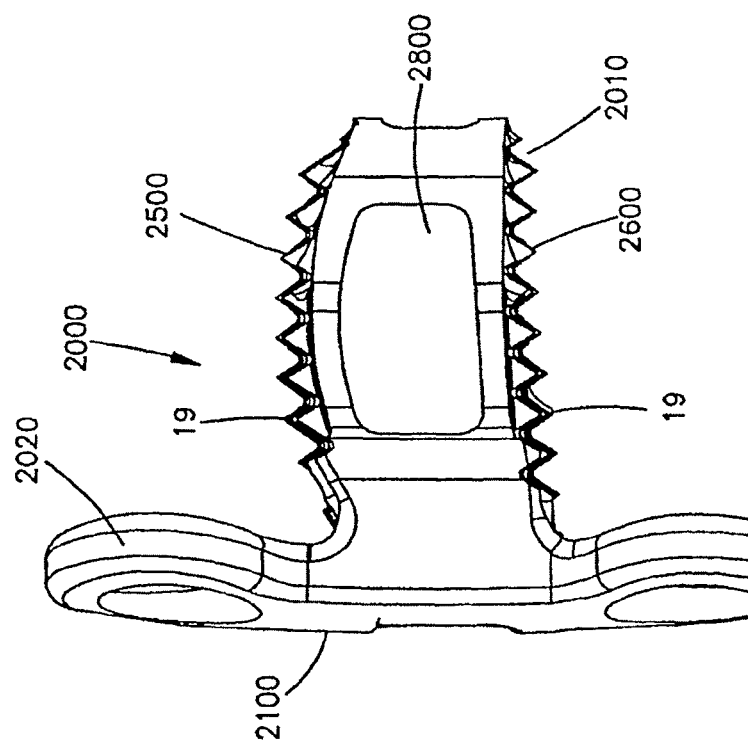

FIGS. 14A-F depict a cervical spacer-plate implant 2000. FIG. 14A is a perspective view of the implant 2000, whereas FIGS. 14B-E are various plane views of the implant. In this embodiment, the plate 2020 and spacer 2010 are integrally formed. The implant 2000 may have an arcuate front face 2100, whereas the end face 2200 of the implant may be plane or arcuate. The implant 2000 may also have arcuate first and second lateral surfaces 2300, 2400, respectively, and an upper surface and a lower surface 2500, 2600. The upper surface 2500 may be arcuate to conform to the contour of the endplate of the upper vertebra. The lower surface 2600 is generally a substantially flat planar surface. The distance between the upper and lower surfaces 2500, 2600 at the front face 2100 may be greater than at the end face 2200. The front face 2100 may be wider than the end face 2200 such that the first and second lateral surfaces 2300, 2400, connected to the front and end faces 2100, 2200 are further apart from each other at the front face than at the end face. The implant 2000 may include one or more openings designed to receive bone graft material. In particular, one or more vertical windows/channels 2700 may extend through the implant from the lower surface 2600 to the upper surface 2500. In some embodiments, the implant 2000 may also have one or more horizontal channels 2800 extending from the first lateral surface 2300 to the second lateral surface 2400, and/or from the front face 2100 to the end face 2200.

Figure 14F:
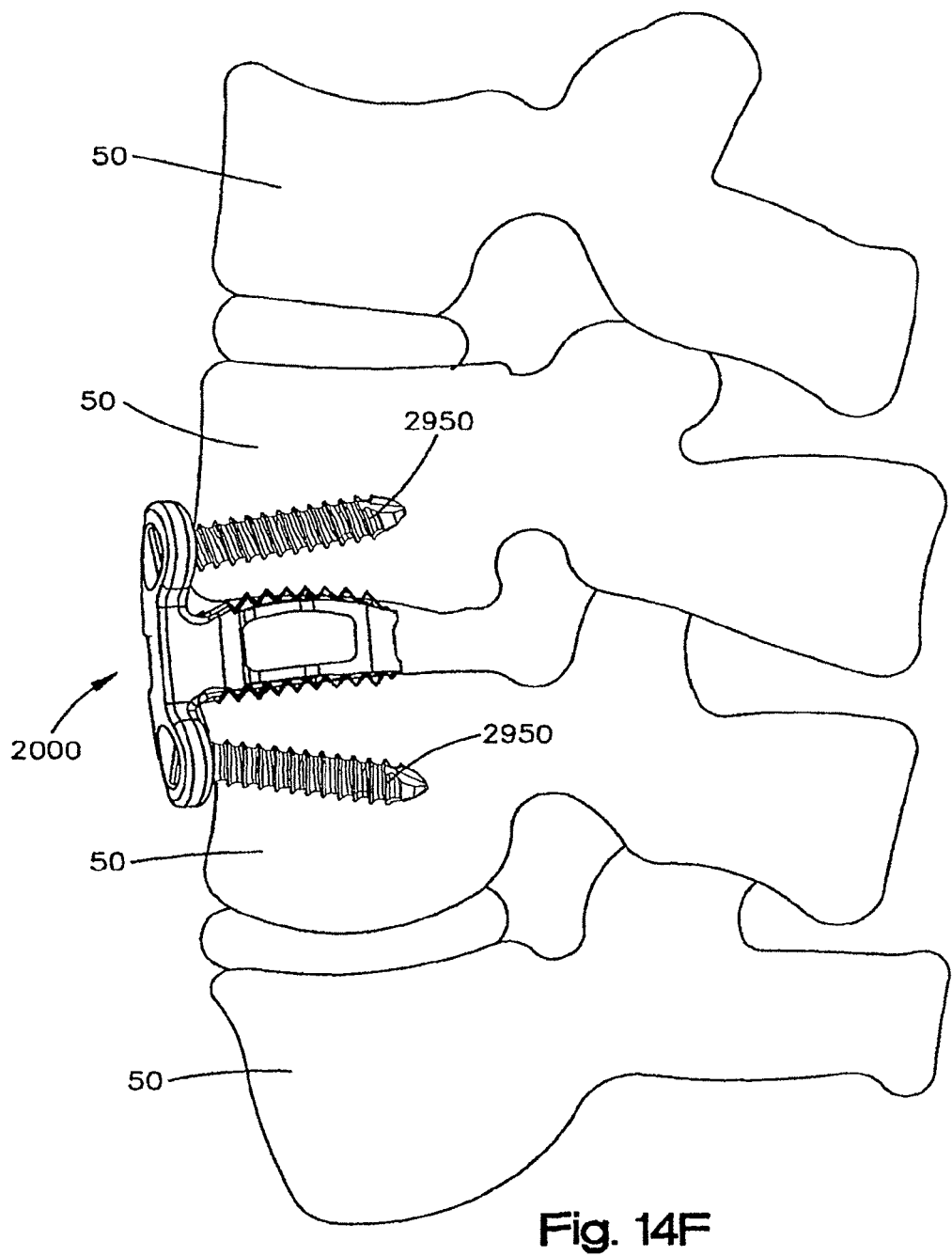
FIG. 14F is a side view of the implant depicted in FIG. 14A, in position between adjacent vertebrae.

The front face 2100 has a height greater than the height of the spacer 2010 to accommodate a retention feature provided by opposing screw fixation. As shown, four holes 2900 accept four fixation screws 2950 which penetrate the vertebral bodies 50 and secure the implant 2000 in place, as shown in FIG. 14F. The holes 2900 form an angle α with respect to the upper and lower surfaces 2500, 2600 of the implant 2000, where the angle may range between 20° and 50°, and preferably ranges between 30° and 45°. The angle α may be the same for all holes or may be different for each hole. After the implant 2000 is placed between adjacent vertebrae 50, screws 2950 are inserted through the holes 2900 to penetrate the vertebrae and hold the implant in position. As with previous embodiments, the upper and/or lower surfaces 2500, 2600 of the implant may include a series of teeth 19, or similar projections, to aid in securing the implant to the vertebral endplates. It is also contemplated that the upper and/or lower surfaces 2500, 2600 may be smooth, having ridges that run laterally with respect to the spacer 2010, or ridges running from the front face 2100 to the end face 2200. The implant 2000 may be formed of PEEK, titanium, titanium alloy, stainless steel, allograft bone, or any other suitable, biocompatible material, or any combination thereof, while screws 2950 may be formed of titanium, titanium alloy or stainless steel.

It should be noted that the screw holes provided in the plates of the embodiments of FIGS. 2-14 may be threaded or smooth, and the screw inserted through the plate may have a head that also may be threaded or smooth. In the embodiment where the screw holes are threaded the heads of the screws are also preferably threaded so that the screw will lock with the plate forming a relatively rigid construct.

Reference is now made to FIGS. 15A-D, which shows an intervertebral implant 70 according to still another preferred embodiment of the present invention. FIG. 15A is a perspective view of the implant, while FIGS. 15B-D are plane views of the implant. In this embodiment, a pair of opposing dovetail keels 72 on the upper and lower surfaces 71, 73 of the implant 70 provide the retention feature. The implant may have arcuate anterior and posterior faces, both curved in the same direction to form a generally kidney bean shape. The keel is generally centrally located and preferably extends about 50 percent the length of the superior and inferior surfaces in an anterior to posterior direction, and more preferably about 80 to about 95 percent of the length in the anterior to posterior direction. The dovetail shape of the keel 72 preferably assists in retaining the implant 100 in position and helps to prevent expulsion of the implant. In particular, the dovetail shape will help to retain contact between the upper and lower surface of the implant and the end plates of the vertebrae. The dovetail shape may also be configured to provide compression. The shape of the implant 70 is generally preferred for the lumbar region of the spine.

No additional plates or screws may be necessary. Implant 70 may be formed of PEEK, titanium, titanium alloy, stainless steel, allograft bone, or any other suitable, biocompatible material, or any combination thereof. Implant 70 may include one or more openings designed to receive bone graft material. In particular, one or more vertical windows/channels 75 may extend through the implant 70 from the lower surface 73 to the upper surface 71. In some embodiments, the implant 70 may also have one or more horizontal channels 74 extending from a first lateral surface 77 to a second lateral surface 78, and/or from the front face 79*a* to the end face 79*b*.

Figure 16A:
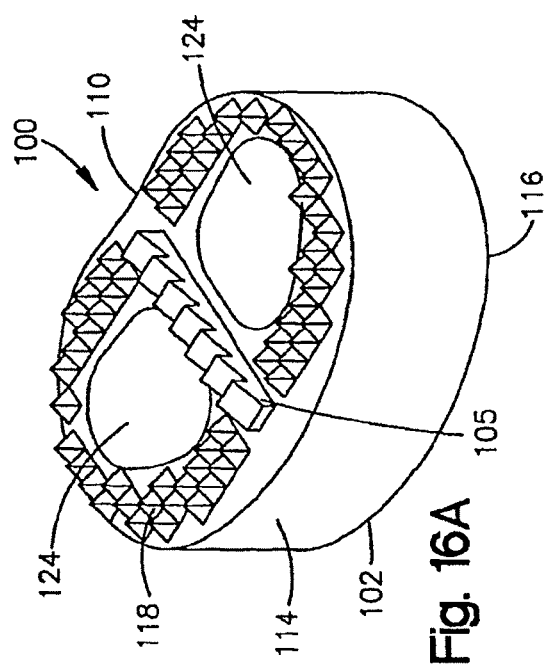
FIG. 16A is a perspective view of an intervertebral implant employing top and bottom keels according to yet another embodiment of the present invention.
Figure 16B:
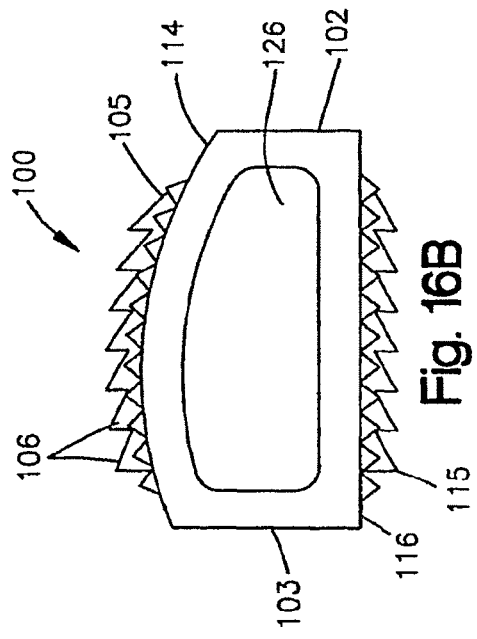
FIG. 16B is a side view of the implant depicted in FIG. 16A.

The implant 100, shown in FIGS. 16A and B, may have arcuate anterior and posterior faces 110, 112, respectively. Superior and inferior faces, 114, 116, respectively, may have projections or teeth 118 for engaging the adjacent vertebrae and aiding in securing the implant 100 in the disc space. The projections 118 may be pyramidal in shape as shown, or may have other shapes. One or more vertical windows/channels 124, designed to receive bone graft material, may extend through the implant 100 from the inferior face 116 to the superior face 114. In some embodiments, the implant 100 may also have one or more horizontal channels 126 designed to receive bone graft material. The implant also has longitudinal sides 102, 103, wherein a first longitudinal side's 102 height may be, and preferably is, less than the height of the second longitudinal side 103.

The implant 100 further may have a retention feature comprising a first fixation member 105 projecting from the superior face 114 and a second fixation member 115 projecting from the inferior face 116. The first and second fixation members 105, 115 resemble a "keel" such that the keel is oriented from the anterior face 110 to the posterior face 112. The length of the keel may be, and preferably is, greater than the width of the keel, and whose length preferably is 80 to 95 percent of the width of the superior and inferior faces 114, 116. The first and second fixation members 105, 115 have a height greater than the height of the projections or teeth 118. The first and second fixation members 105, 115 may have projections 106, such as in the form of a saw-tooth, for engaging the adjacent vertebrae and aiding in securing the implant 100 in the disc space without the need for supplemental fixation means. The saw-tooth shape of the projections allows the implant to be inserted while requiring a larger force for the implant to be removed from between vertebrae. The keel also helps prevent rotation or turning of the implant. No additional plates or screws may be necessary to retain the implant between two vertebrae. Implant 100 may be formed of PEEK, titanium, titanium alloy, stainless steel, allograft bone, or any other suitable, biocompatible material, or any combination thereof.

Figure 17A:
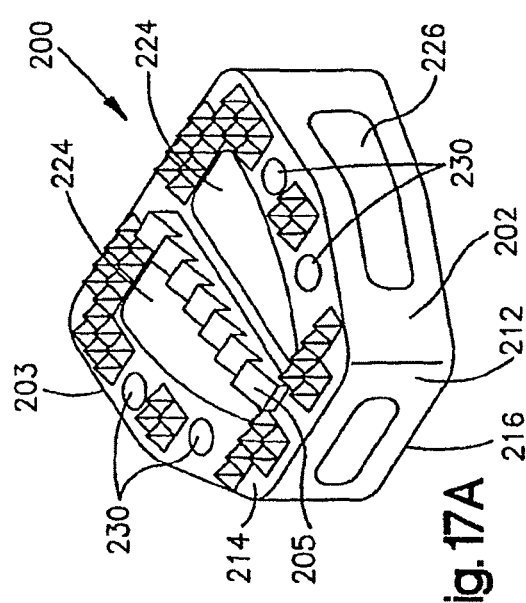
FIG. 17A is a perspective view of an intervertebral implant employing top and bottom keels according to yet another embodiment of the present invention.
Figure 17B:
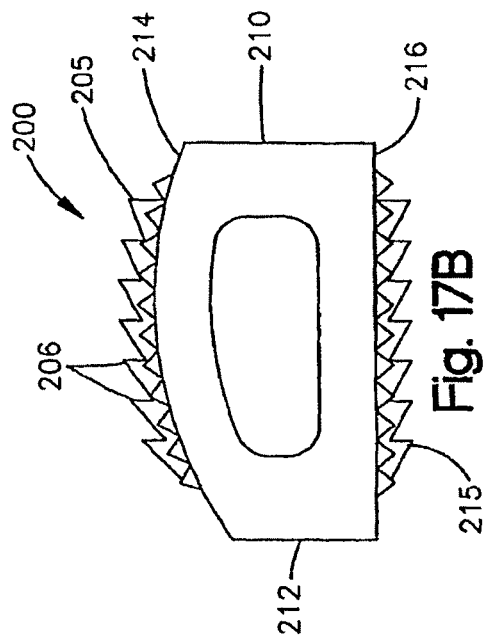
FIG. 17B is a side view of the implant depicted in FIG. 17A.

FIGS. 17A and B depict another embodiment of the implant 200. The implant 100 may have end faces 210, 212, respectively. The end faces 210, 212 may be substantially flat or arcuate shaped. Face 210 may have a greater length than face 212. The implant also may have arcuate first and second longitudinal surfaces 202, 203, respectively, and an inferior face 216 and a superior face 214. One or more vertical windows/channels 224 may extend through the implant 200 from the inferior face 216 to the superior face 214. Additional vertical channels 230, extending from the inferior face 216 to the superior face 214 may be positioned on the perimeter of the superior and inferior faces 214, 216. In some embodiments, the implant 200 may also have one or more horizontal channels 226. The height of the first face 210 may be greater than the height of the second face 212.

The implant 200 further may have a retention feature comprising a first fixation member 205 projecting from the superior surface 214 and a second fixation member 215 projecting from the inferior surface 216. The first and second fixation members 205, 215 resemble a "keel" such that the keel is oriented from face 210 to face 212. The length of the keel may be, and preferably is, greater than the width of the keel, and whose length preferably is 80 to 95 percent of the length of the superior and inferior faces 214, 216. The first and second fixation members 205, 215 may have projections 206, such as in the form of a saw-tooth, for engaging the adjacent vertebrae and aiding in securing the implant 200 in the disc space, preferably without the need for supplemental fixation means. No additional plate or screws may be necessary to retain the implant between two vertebrae. Implant 200 may be formed of PEEK, titanium, titanium alloy, stainless steel, allograft bone, or any other suitable, biocompatible material, or any combination thereof.

The intervertebral implant 300, shown in FIG. 18, has arcuate end faces 310, 312, respectively. Superior and inferior faces, 314, 316, respectively, which may be curved and may have projections or teeth 318 for engaging the adjacent vertebrae and aiding in securing the implant 300 in the disc space. The projections 318 may be pyramidal in shape. The implant also has longitudinal sides 302, 303. The intervertebral implant 300 of this embodiment differs from the implant 100 in that intervertebral implant 300 has no horizontal or vertical channels, such that superior and inferior faces 314, 316 and longitudinal surfaces 302, 303 has no openings.

The implant 300 further has a retention feature comprising a first fixation member 305 projecting from the superior face 314 and a second fixation member 315 projecting from the inferior face 316. The first and second fixation members 305, 315 resemble a "keel" such that the keel is oriented from front face 310 to end face 312. The length of the keel may be, and preferably is, greater than the width of the keel, and whose length is 80 to 95 percent of the width of the superior and inferior faces 314, 316. The first and second fixation members 305, 315 have a height greater than the height of the projections or teeth 318. The first and second fixation members 305, 315 may have projections 306, such as in the form of a saw-tooth, for engaging the adjacent vertebrae and aiding in securing the implant 300 in the disc space, preferably without the need for supplemental fixation means. No additional plate or screws may be necessary to retain the implant between two vertebrae. Implant 300 may be formed of PEEK, titanium, titanium alloy, stainless steel, allograft bone, or any other suitable, biocompatible material, or any combination thereof.

FIG. 19 depicts yet another embodiment of an implant 400 having first and second fixation members 405, 415 that resemble a "keel" such that the keel is oriented from front face 410 to end face 412. The first and second fixation members 405, 415 may have generally parallel side walls 416, 417 from the front towards the rear or end of the fixation members 405, 415. The side walls 416, 417 of the first and second fixation members 405, 415 near the end of the keel may be angled towards each other forming a wedge 418 at the end of the members 405, 415. The wedge 418 may allow for easier insertion between two vertebrae 50. The length of the keel may be, and preferably is, greater than the width of the keel, and whose length is 80 to 95 percent of the width of the superior and inferior faces 414, 416. The first and second fixation members 405, 415 have a height greater than the height of the projections or teeth 418. The first and second fixation members 405, 415 may include a recess 422. The recess 422 may be sized to fit an insertion tool (not shown), such that the front 420 of the first and second fixation member 405, 415 have an opening allowing the insertion tool to grip the implant 400 for insertion between two vertebrae. Implant 400 may be formed of PEEK, titanium, titanium alloy, stainless steel, allograft bone, or any other suitable, biocompatible material, or any combination thereof.

The implants described herein are generally sized and configured for anterior insertion, although different configurations may be possible for posterior approaches. In addition to the features shown the implants, spacers, and plate/spacer constructs may have threaded holes, slots or channels to mate with instruments to facilitate holding and inserting the implants.

Although the present invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art. For example, the present invention may be employed in different sections of the spinal column, including, but not limited to, the cervical area.

What is claimed is:

1. An intervertebral implant for implantation in a treated area of an intervertebral space between first and second vertebral bodies of a spine, the intervertebral implant comprising:
   a spacer having an inferior and a superior surface, an anterior surface, a posterior surface, a first lateral side surface and a second lateral side surface, wherein the inferior and superior surfaces each have a contact area configured to engage with the first and second vertebral bodies, respectively, when the spacer is inserted into the intervertebral space in an insertion direction; and
   first and second blades that are rotatable relative to the spacer so as to penetrate into the first and second vertebral bodies, respectively, wherein the first and second blades define a rearmost surface of the implant with respect to the insertion direction.

2. The intervertebral implant of claim 1, wherein the blades are wedge-shaped.

3. The intervertebral implant of claim 1, wherein the blades define tips that are pointed in opposite directions.

4. The intervertebral implant of claim 1, wherein the blades are rotatable about an axis that is oriented along a direction that separates the anterior surface from the posterior surface.

5. The intervertebral implant of claim 1, further comprising a hub that is configured to engage a tool that drives the blades to rotate.

6. The intervertebral implant of claim 1, wherein the blades comprise a metal.

7. The intervertebral implant of claim 1, wherein the blades are configured to rotate 90 degrees so as to penetrate into the first and second vertebral bodies, respectively.

8. The intervertebral implant of claim 1, wherein each of the superior surface and the inferior surface of the spacer comprises teeth.

9. The intervertebral implant of claim 1, further comprising a plate coupled to the spacer, wherein the blades are further configured to rotate relative to the plate.

10. The intervertebral implant of claim 9, wherein the plate comprises a metal, and the spacer comprises a polymer.

11. A method of fusing first and second vertebral bodies of a spine to each other, the method comprising the steps of:
    inserting a spacer of an intervertebral implant in an insertion direction into an intervertebral space defined by the first and second vertebra bodies, such that respective inferior and superior surfaces of the spacer engage with the first and second vertebral bodies, respectively; and
    rotating first and second blades of the intervertebral implant relative to the spacer so as to penetrate into the first and second vertebral bodies, respectively, wherein the first and second blades define a rearmost surface of the implant with respect to the insertion direction.

12. The method of claim 11, wherein the blades are wedge-shaped.

13. The method of claim 11, wherein the blades define tips that are pointed in opposite directions.

14. The method of claim 11, wherein the rotating step comprises rotating the first and second blades about an axis that is oriented along a direction that separates an anterior surface of the spacer from a posterior surface of the spacer.

15. The method of claim 11, wherein the rotating step further comprises engaging a tool with a hub of the intervertebral implant and applying a rotative force to the hub.

16. The method of claim 11, wherein the blades comprise a metal.

17. The method of claim 11, wherein the rotating step comprises rotating the blades 90 degrees so as to penetrate into the first and second vertebral bodies, respectively.

18. The intervertebral implant of claim 11, further comprising the step of engaging the first and second vertebral bodies with teeth that extend out from the superior surface and inferior surface, respectively.

* * * * *